(12) United States Patent
Lu et al.

(10) Patent No.: US 8,242,253 B2
(45) Date of Patent: Aug. 14, 2012

(54) NUCLEOTIDE SEQUENCE OF SHRIMP ACTIN PROMOTER AND ITS USE IN GENETIC TRANSFORMATION BIOTECHNOLOGY

(76) Inventors: Yuanan Lu, Honolulu, HI (US); Marcus Soderlund, Honolulu, HI (US)

( * ) Notice: Subject to any disclaimer, the term of this patent is extended or adjusted under 35 U.S.C. 154(b) by 891 days.

(21) Appl. No.: 12/274,627

(22) Filed: Nov. 20, 2008

(65) Prior Publication Data

US 2009/0133139 A1   May 21, 2009

Related U.S. Application Data

(60) Provisional application No. 60/989,189, filed on Nov. 20, 2007.

(51) Int. Cl.
*C07H 21/04* (2006.01)
*C12N 15/63* (2006.01)
*C12N 15/86* (2006.01)
*C12N 5/10* (2006.01)

(52) U.S. Cl. ............ 536/24.1; 435/320.1; 435/325

(58) Field of Classification Search .......... 536/24.1; 435/320.1, 325
See application file for complete search history.

(56) References Cited

U.S. PATENT DOCUMENTS

| 7,115,794 | B2 | 10/2006 | Sun |
| 2004/0177392 | A1 | 9/2004 | Barratt et al. |
| 2004/0250308 | A1 | 12/2004 | Sun |
| 2006/0242719 | A1 | 10/2006 | Sun |

FOREIGN PATENT DOCUMENTS

WO    03/048325 A2    6/2003

OTHER PUBLICATIONS

Preston et al. (2000) Aquaculture, vol. 181: 225-234.*
Bachere et al. (Dec. 1997) World Aquaculture, 51-55.*
Namikoshi et al. (2004) Aquaculture, vol. 229, 25-35.*
International Search Report for International Patent Application No. PCT/US08/84154 (Mar. 10, 2009).
Lu et al., "Viral Resistance in Shrimp that Express an Antisense Taura Syndrome Virus Coat Protein Gene," Antiviral Research 67:141-6 (2005).
Sun et al., "Evaluation of Methods for DNA Delivery into Shrimp Zygotes of Penaeus (Litopenaeus) Vannamei," Aquaculture 243:19-26 (2005).
Written Opinion of the International Searching Authority for International Patent Application No. PCT/US08/84154 (Jan. 29, 2009).
Sun, P. et al. "Isolation and characterization of two actins of the Pacific white shrimp, Litopenaeus vannamei," Marine Biology 151(6):2145-2151(7)(2007).
GenBank Accession No. AF300705, Litopenaeus vannamei beta-actin mRNA, complete cds.

* cited by examiner

*Primary Examiner* — Anne Marie S Wehbe
(74) *Attorney, Agent, or Firm* — Nixon Peabody LLP

(57) ABSTRACT

The present invention relates to an isolated β-actin nucleic acid promoter molecule from shrimp; nucleic acid constructs including the β-actin promoter molecule; and expression vectors, host cells, and transgenic animals transduced with the isolated β-actin nucleic acid promoter. Also disclosed are methods for imparting to an animal resistance against a pathogen, regulating growth of an animal, increasing stress tolerance in an animal, and increasing cold tolerance in an animal that involves transforming an animal with a nucleic acid construct including the isolated β-actin nucleic acid promoter molecule of the present invention.

13 Claims, 10 Drawing Sheets

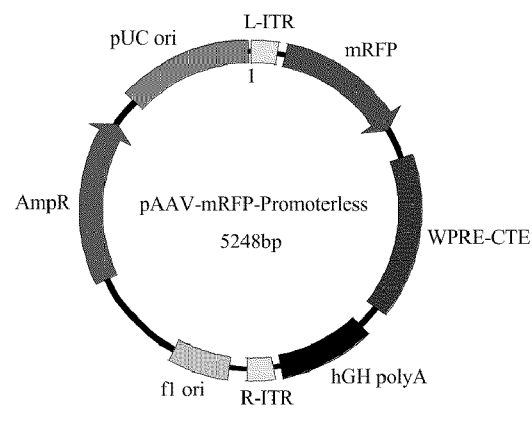 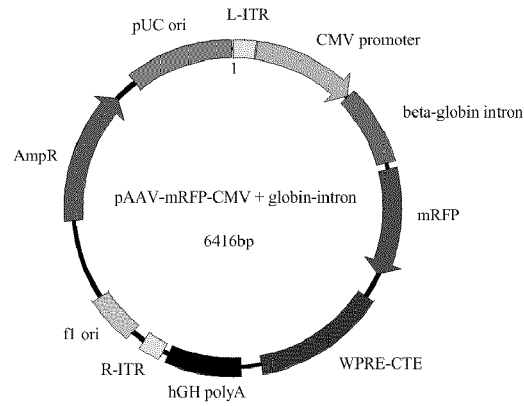
Negative Control Plasmid (promoterless)
CMV Promoter
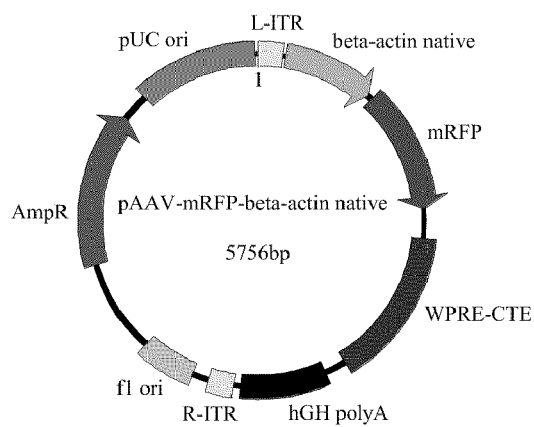 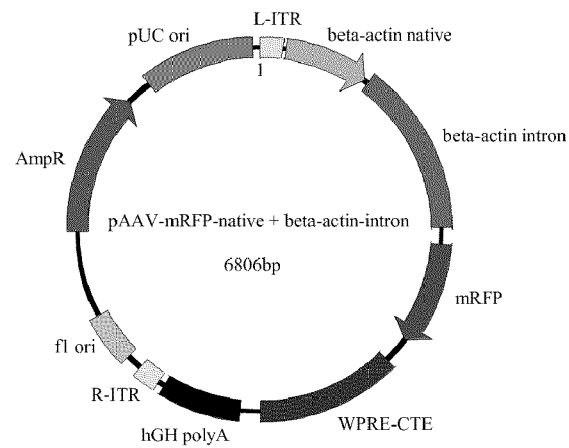
Beta-actin beta-actin-native (no intron)
Shrimp Promoter (Native)
Figures 7A-D (CCO cells)

(EPC cells)

(CHSE-214 cells)

NUCLEOTIDE SEQUENCE OF SHRIMP ACTIN PROMOTER AND ITS USE IN GENETIC TRANSFORMATION BIOTECHNOLOGY

This application claims the priority benefit of U.S. Provisional Patent Application Ser. No. 60/989,189, filed Nov. 20, 2007, which is hereby incorporated by reference in its entirety.

FIELD OF THE INVENTION

The present invention relates to an isolated β-actin nucleic acid promoter molecule from shrimp and its use in genetic transformation biotechnology.

BACKGROUND OF THE INVENTION

Infectious diseases among shrimp have taken a devastating toll on aquaculture production. Among the most harmful pathogens are viruses, bacteria, and protozoans, with viruses posing the greatest threat to shrimp survival rates. Bacterial and fungal infections in shrimp can usually be controlled effectively by applying available chemical treatments to shrimp populations in hatchery ponds or tanks. However, there are currently no effective chemicals or antibiotics to treat viral diseases. Other strategies used in handling shrimp disease problems include immunostimulation, vaccination, quarantine, and environmental management. These strategies are generally targeted at three elements: pathogens, host, and environment. Boosting the shrimp's natural defense system against pathogens is a non-specific approach to combating disease which does not improve the shrimp's ability to cope with future outbreaks of the same disease since shrimp and other invertebrates lack a memory immune response based on antibody production. The lack of basic information about shrimp immunology is also another impediment to the development of efficient strategies for combating viral diseases via traditional methods.

Viral diseases are the most devastating problem facing shrimp aquaculture. The four major viruses, including white spot syndrome virus (WSSV), yellow head virus (YHV), Taura syndrome virus (TSV), and infectious hypodermal and hematopoietic necrosis virus (IHHNV), pose the greatest threat to penaeid shrimp farming worldwide. The IHHNV was first detected in Hawaii in 1981, causing up to 90% mortality in juvenile shrimp, *Litopenaeus stylirostris* (Lightner et al., "Infectious Hypodermal and Hematopoietic Necrosis, a Newly Recognized Virus Disease of Penaeid Shrimp," *J. Invert. PathoL* 42: 62-70 (1983)). This virus has since been reported to infect most *Litopenaeus* species (which was previously known as the *Penaeus* species), including the Pacific white shrimp, *L. vannamei* and the blue shrimp, *L. stylirostris*, causing tremendous economic losses worldwide (Brock, "An Overview of Diseases of Cultured Crustaceans in the Asia Pacific Region," in *Fish Health Management in Asia-Pacific. Report on a Regional Study and Workshop on Fish Disease and Fish Health Management*, ADB Agriculture Department Report Series No. 1. Network of Aquaculture Centres in Asia-Pacific. Bangkok, Thailand, pp. 347-395 (1991); Flegel, "Major Viral Diseases of the Black Tiger Prawn (*Penaeus Monodon*) In Thailand," in NRIA International Workshop, *New approaches to viral diseases of aquatic animals*, Kyoto, Japan. Jan. 21-24, 1997, National Research Institute of Aquaculture, Nansei, Mie 516-01, Japan pp. 167-189 (1997)). TSV has infected United States farms rearing *Litopenaeus vannamei* since 1992 and has caused more than 2 billion dollars in damage to aquaculture farms (Brock, "An Overview of Taura Syndrome, an Important Disease of Farmed *Penaeus Vannamei*," in C. L. Browndy and J. S. Hopkins, (eds.), *Swimming Through Troubled Water. Proceedings of the Special Section on Shrimp Farming*, Baton-Rouge, La.: World Aquaculture Society pp. 84-94 (1995); Lightner et al., "Risk of Spread of Penaeid Shrimp Viruses in the Americas by the International Movement of Live and Frozen Shrimp," *Rev. Sci. Tech.* 16(1):146-60 (1997)). In Hawaii, both TSV and IHHNV infections in shrimp farms have been frequently reported since 1994 (MacMillan, "Shrimp Diseases in Hawaii, USA". UNIHI-SG-FS-96-02. University of Hawaii Sea Grant College Program, Honolulu (1996)). Controlling viral diseases clearly represents a great challenge as there are currently no effective chemicals or antibiotics to treat viral infection. The serious effects of viral disease outbreaks among cultured shrimp coupled with a decline in natural fisheries of healthy shrimp (Pullin et al., "Domestication of Crustaceans," *Asian Fisheries Sci.* 11(1): 59-69 (1998)), have led to a critical demand for advanced biotechnological applications.

The two major penaeid shrimp species cultured in the Americas, *L. vannamei* and *L. Stylirostris*, have differing susceptibilities to TSV and IHHNV. *L. vannamei* is more resistant to IHHNV, but susceptible to TSV, whereas *L. stylirostris* is innately resistant to TSV but highly susceptible to IHHNV (Lightner et al., "Strategies for the Control of Viral Diseases of Shrimp in the Americas," *Fish Pathology* 33:165-180 (1998)). Despite the relative resistance of *L. vannamei* to IHHNV, runt deformity syndrome (RDS) was still observable in this shrimp species when exposed to IHHNV. Although these viral diseases may not be completely fatal, the reduced growth rate resulting from viral-induced RDS results in immense revenue losses for shrimp farmers each year.

Systematic genetic selection is known to enhance disease resistance in a number of farmed plants and animals, including fish (Gjedrem et al., "Genetic Variation in Susceptibility of Atlantic Salmon to Furunculosis," *Aquaculture* 97:1-6 (1991)). However, the efficacy of breeding for disease resistance in penaeid shrimp is not well established because of the paucity of information about relevant genetic parameters, such as phenotypic and genetic variation, heritability, and genetic correlations between traits. In response to viral-disease problems facing the shrimp farming industry, the U.S. Marine Shrimp Farming Program (USMSFP), with funding from USDA/CSREES, has developed a selective breeding program to enhance disease resistance and improve growth in *L. vannamei* (Moss et al., "Breeding for Disease Resistance in Penaeid Shrimp: Experiences From the U.S. Marine Shrimp Farming Program," In: Proceedings of the 1$^{st}$ Latin American Shrimp Farming Congress (D. E. Jory, ed.), Panama City, Panama, 9 pp. (1998); Argue et al., "Selective Breeding of Pacific White Shrimp (*Litopenaeus Vannamei*) for Growth and Resistance to Taura Syndrome Virus," *Aquaculture* 204: 447-460 (2002)). Although high between-family variation in response to TSV challenge was observed in all groups of shrimp tested, heritability estimates ($h^2$) for TSV resistance were low ($h^2_{full-sib}$=0.14). Heritability describes the percentage of phenotypic variance that is inherited in a predictable manner and is used to determine the potential response to selection (Tave, "Genetics for Fish Hatchery Managers," 2nd ed., AVI, New York, 415 pp (1993)). Estimates of $h^2$ typically are low for fitness traits, such as disease resistance, and phenotypes with $h^2 \leq 0.15$ are difficult to improve by selection. Although the development of TSV-resistant strains of *L. vannamei* have benefited shrimp farmers, breeding for TSV resistance is not a panacea to the health problems plaguing the industry. Viruses can mutate, thereby rendering selectively bred shrimp incapable of defending themselves against new strains of virus. Furthermore, TSV resistance could be negatively correlated with resistance to other pathogens. There is also the potential to produce shrimp that respond well in disease-challenge tests used in breeding programs, but perform poorly when stocked in commercial ponds.

The use of molecular biology techniques to produce pathogen-resistant strains of shrimp through genetic transformation technology is considered a highly promising strategy for control of shrimp viral disease (Mialhe et al., "Future of Biotechnology-Based Control of Disease in Marine Invertebrates," *Mol. Mar. Biol. and Biotechnol.* 4(4):275-83 (1995); Bachere et al., "Transgenic Crustaceans," *World Aquaculture* 28(4):51-5 (1997)). In the past decade, pathogen-resistant transgenic animals and plants have been developed (Beachy, "Virus Cross-Protection in Transgenic Plants," in D. P. S. Verma, and R. B. Goldberg, (eds.), *Plant Gene Research: Temporal and Spatial Regulation of Plant Genes*, New York: Springer Verlag pp. 313-327 (1998); Kim et al., "Disease Resistance in Tobacco and Tomato Plants Transformed with the Tomato Spotted Wilt Virus Nucleocapsid Gene," *Plant Dis.* 78:615-21 (1993); Sin, "Transgenic Fish," *Rev. Fish Biol.* 7(4):417-41 (1997)), but use of such technology has only just begun for shrimp research. While methods for detecting viral disease in shrimp, including polymerase chain reaction (Dhar et al., "Detection and Quantification of Infectious Hypodermal and Hematopoietic Necrosis Virus (IHHNV) and White Spot Virus (WSV) of Shrimp by Real-Time Quantitative PCR and SYBR Chemistry," *J. Clin. Microbiol.* 39:2835-2845 (2001); Tang et al., "Detection and Quantification of Infectious Hypodermal and Hematopoietic Necrosis Virus in Penaeid Shrimp by Real-Time PCR," *Dis. Aquat. Org.* 44(2): 79-85 (2001)), light microscopy, and transmission electron microscopy (Nunan et al., "Reverse Transcription Polymerase Chain Reaction (RT-PCR) Used for the Detection of Taura Syndrome Virus (TSV) in Experimentally Infected Shrimp," *Dis. Aquatic. Org.* 34:87-91 (1998); Goarant et al., "Arbitrarily Primed PCR to Type Vibrio Spp. Pathogenic for Shrimp," *Appl. Environ. Microbiol.* 65(3):1145-1151 (1999); Chen et al., "Establishment of Cell Culture Systems from Penaeid Shrimp and Their Susceptibility to White Spot Disease and Yellow Head Viruses," *Meth, in Cell Sci.* 21:199-206 (1999); Toullec, "Crustacean Primary Cell Culture: a Technical Approach," *Meth. In Cell Sci.* 21:193-8 (1999); Sukhumsirichart et al., "Characterization and PCR Detection of Hepatopancreatic Parvovirus (HPV) from *Penaeus Monodon* in Thailand," *Dis. Aquat. Org.* 38:1-10 (1999) are widely used, these methods for controlling viral disease in shrimp are still in development. The first studies on genetic transformation of marine molluscs and shrimp were initiated in 1988 in France at IFREMER, in the United States at the University of Maryland Biotechnology Institute, and in Australia at CSIRO. A few studies on the introduction of foreign DNA into shrimp embryos via transfection methods have obtained preliminary data demonstrating transient expression of a reporter gene by heterologous promoters (Gendreau et al., "Transient Expression of a Luciferase Reporter Gene After Ballistic Introduction Into *Artemia franciscana* (Crustacea) Embryos," *Aquaculture* 133:199-205 (1995)). Recent advances in gene transfer technology such as these hold immense potential for developing transgenic shrimp harboring genes that convey viral disease resistance or enhance shrimp growth rates. Gene transfer technology thus represents a practical alternative to the lengthy and expensive selective breeding process (Wolfus et al., "Application of the Microsatellite Technique for Analyzing Genetic Diversity in Shrimp Breeding Programs," *Aquaculture* 152:35-47 (1997)) and provides a powerful tool for revolutionizing not only shrimp aquaculture, but also livestock husbandry in general.

Construction of an effective expression vector is an important step toward implementing the genetic transformation process in animals. The expression vector is generally composed of three elements: a promoter, a target gene, and a region having transcriptional termination signals. Among these three components, a suitable promoter is an essential element for a successful gene transformation system. The promoter determines where, when, and under what conditions the target gene should be turned on.

A suitable promoter that is appropriate for aquaculture and acceptable to consumers should ideally be derived from marine origin and should not pose any potential health hazards. Several fish gene promoters have been successfully isolated and used to drive foreign gene expression in fish (Jankowski et al., "The GC Box as a Silencer," *Biosci. Rep.* 7:955-63 (1987); Zafarullah et al., "Structure of the Rainbow Trout Metallothionein B Gene and Characterization of its Metal-Responsive Region," *Mol. Cell. Biol.* 8:4469-76 (1988); Liu et al., "Development of Expression Vectors for Transgenic Fish," *Bio/Technology* 8:1268-1272 (1990b); Gong et al., "Functional Analysis and Temporal Expression of Promoter Regions From Fish Antifreeze Protein Genes in Transgenic Japanese Medaka Embryos," *Mol. Mar. Biol. Biotechnol.* 1(1):64-72 (1991); Du et al., "Growth Enhancement in Transgenic Atlantic Salmon by the Use of Fish Antifreeze/ Growth Hormone Chimeric Gene Constructs," *Biotechnology* 10:176-81 (1992); Gong et al., "Transgenic Fish in Aquaculture and Developmental Biology," *Current Topic in Develop. Biol.* 30:175-213 (1995); Chen et al., "Transgenic Fish and Aquaculture," *Biotechnol. Apl.* 13(1):50 (1996); Chan et al., "PCR Cloning and Expression of the Molt-Inhibiting Hormone Gene for the Crab (*Charybdis feriatus*)," *Gene* 224:23-33 (1998); Gong, "Zebrafish Expressed Sequence Tags and Their Applications," *Meth. Cell Biol.* (zebrafish volume) 60:213-233 (1998); Ju et al., "Faithful Expression of Green Fluorescent Protein (GFP) in Transgenic Zebrafish Embryos Under Control of Zebrafish Gene Promoters," *Dev. Genet.* 25(2):158-67 (1999); Yoshizaki et al., "Germ Cell-Specific Expression of Green Fluorescent Protein in Transgenic Rainbow Trout Under Control of the Rainbow Trout Vasa-Like Gene Promoter," *Int. J. Dev. Biol.* 44(3):323-6 (2000)). Other promoters used to date in transgenic marine fish include mouse metallothionein (McEvoy et al., "The Expression of a Foreign Gene in Salmon Embryos," *Aquaculture* 68:27-37 (1988); Rahman et al., "Fish Transgene Expression by Direct Injection Into Fish Muscle," *Mol. Mar. Biol. Biotechnol.* 1:286-289 (1992)), heat shock promoters (Bayer et al., "A Transgene Containing lacZ is Expressed in Primary Sensory Neurons in Zebrafish," Development 115: 421-446 (1992); Krone, "Several Unique Hsp 90 Genes are Expressed During Embryonic Development of Zebrafish," Presented at *Symposium on Advances in Molecular Endocrinology of Fish*, May 23-25, Toronto, Canada (1993)), chicken β-actin promoter (Lu et al., "Integration and Germline Transmission of Human Growth Hormone Gene in Medaka (*Oryzias latipes*)," presented at *Second International Marine Biotechnology Conference*, 1991, Baltimore, Md. (1991); Inoue et al., "Introduction, Expression, and Growth-Enhancing Effect of Rainbow Trout Growth Hormone cDNA Fused to an Avian Chimeric Promoter in Rainbow Fry," *J. Mar. Biotechnol.* 1:131-4 (1993)), carp β-actin promoter (Liu et al., "Functional Analysis of Elements Affecting Expression of the β-Actin Gene of Carp," *Mol. Cell Biol.* 10:3432-3440 (1990); Rahman et al., "Fish Transgene Expression by Direct Injection Into Fish Muscle," *Mol. Mar. Biol. Biotechnol.* 1:286-289 (1992)), the antifreeze protein promoter from the ocean pout (*Macrozoarces americanus*) (Gong et al., "Functional Analysis and Temporal Expression of Promoter Regions From Fish Antifreeze Protein Genes in Transgenic Japanese Medaka Embryos," *Mol. Mar. Biol. Biotechnol.* 1(1):64-72 (1991); Hew et al., "Antifreeze Protein Gene Transfer in Atlantic Salmon," Presented at Second International Marine Biotechnology Conference, 1991, Baltimore, Md. (1991); Du et al., "Growth Enhancement in Transgenic Atlantic Salmon by the Use of Fish Antifreeze/Growth Hormone Chimeric Gene Constructs," *Biotechnology* 10:176-81 (1992)), and the histone promoter from the trout (Muller et al., "Introducing Foreign Genes Into Fish Eggs With Electroporated Sperm as a Carrier," *Mol. Mar. Biol. Biotechnol.* 1:276-281 (1992)). Unfortunately, these promoters have disadvantages, including inconsistent transgenic expression, potential toxicity due to their viral origin, and association with metabolic poisons and/or tumor-inducing sequences, all of which will present major stumbling blocks toward attaining FDA approval for the commercial use of transgenic animals. However, isolation and use of promoter genes from crustacean shrimp has not been reported. Thus, the tremendous potential presented by gene transfer technology has not yet been realized in shrimp aquaculture due to the lack of a constitutive, non-inducible, and non-developmentally regulated promoter to efficiently drive the expression of heterologous genes in shrimp and other marine animals.

The present invention is directed to overcoming these and other deficiencies in the art.

SUMMARY OF THE INVENTION

The present invention relates to an isolated β-actin nucleic acid promoter molecule from shrimp having a nucleotide sequence which is at least 90% similar to the nucleotide sequence of SEQ ID NO:1.

The present invention also relates to expression vectors, host cells, and transgenic animals transduced with the isolated β-actin nucleic acid promoter molecule from shrimp, and methods for imparting to an animal resistance against a pathogen, regulating growth of an animal, and increasing stress tolerance in an animal, that involve transforming an animal with a nucleic acid construct including the isolated β-actin nucleic acid promoter molecule of the present invention.

Transgenic strains of animals with new and desirable genetic traits may offer great benefits in marine aquaculture. For example, control of infectious diseases and acceleration of growth rate, two of the most important challenges facing commercial shrimp aquaculture today, may be answered by the application of recombinant DNA technology to these problems. However, genetic engineering of shrimp and other crustaceans requires a suitable promoter that, ideally, is constitutive, non-inducible, non-developmentally regulated, and derived from marine origin so as not to pose any potential health hazards. The present invention provides such promoters, and uses advanced recombinant DNA technology to produce transgenic marine animals into which one or more desirable DNA sequences can be introduced.

The present invention relates to the isolated β-actin promoter nucleic acid sequences which include the promoter region, the complete 5' regulatory untranslated region (UTR), the complete 1st intron sequence, and their regulatory elements of transcription located within Pacific white shrimp (*Litopenaeus vannamei*) DNA, hereafter collectively referred to as the promoter and their use in genetic transformation biotechnology.

BRIEF DESCRIPTION OF THE DRAWINGS

FIGS. 7A-D are schematic gene diagrams showing the structure of plasmids. FIG. 7A shows a negative control plasmid (promoterless plasmid backbone). FIG. 7B shows a positive control plasmid with CMV promoter. FIG. 7C shows a plasmid with shrimp beta-actin promoter without intron sequences. FIG. 7D shows a plasmid construct with shrimp promoter and associated intronic transcriptional regulatory elements.

DETAILED DESCRIPTION OF THE INVENTION

Figure 1:
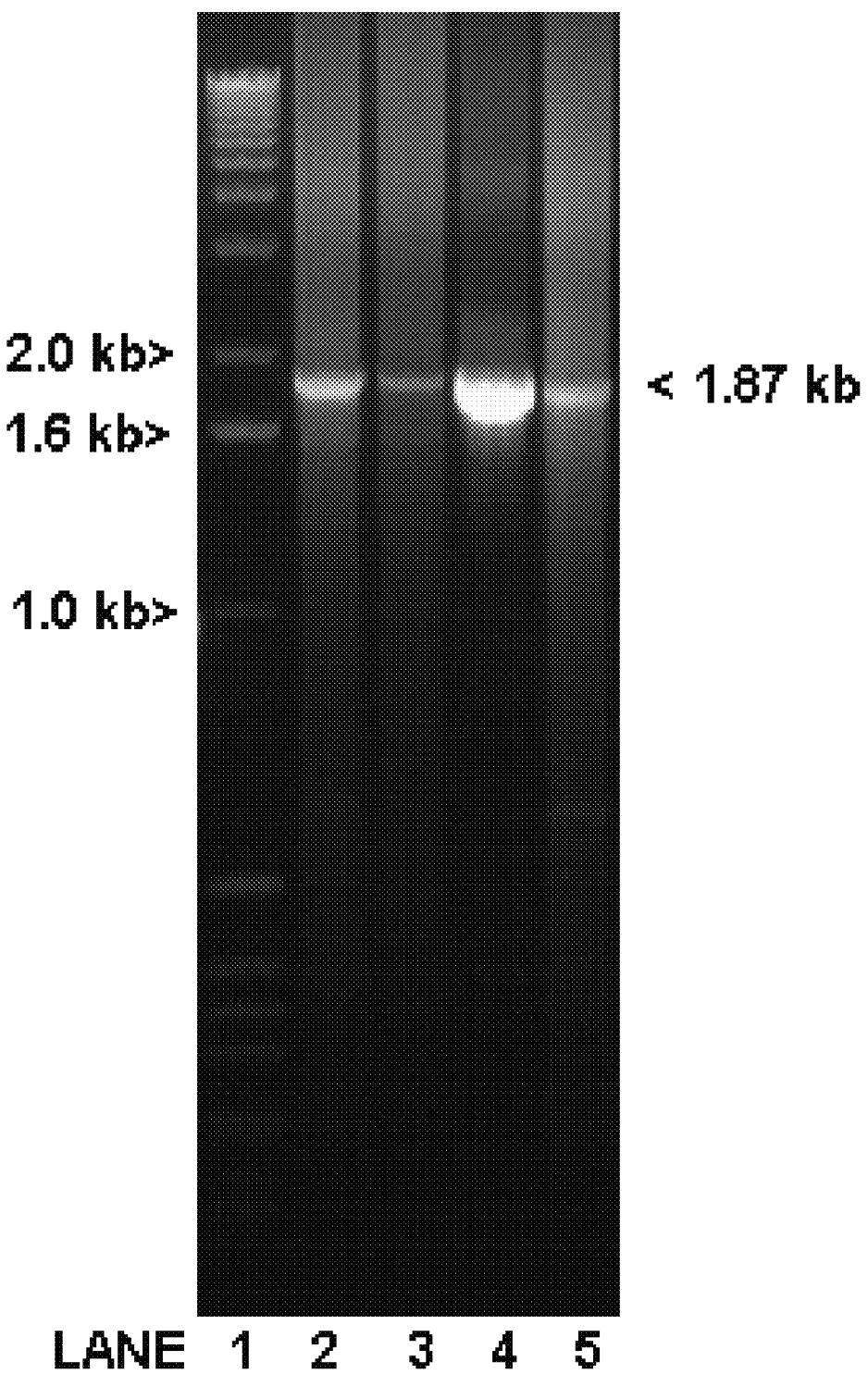
FIG. 1 is an electrophoresis image of PCR amplification of Beta-actin 1st intron and promoter sequences. Lane 1: Invitrogen 1 kb DNA Ladder molecular size standard. Lanes 2, 3, 4, 5: PCR products with an approximate size of 1.87 kb, which were used to sequence part of the 1st intron, were generated using the primers LV-B-act-27-Se (SEQ ID NO:2) and LV-B-act-663-As (SEQ ID NO:3).

The present invention relates to an isolated β-actin nucleic acid promoter molecule from shrimp (*Litopenaeus vannamei*) having a nucleotide sequence of SEQ ID NO:1, as follows:

```
aaaatgaggc ggcggcaatg atttacgggc atatattcgg tcgaggagga cgaaatattc      60
tgaaatggaa cgaaagggga tgacgcggcg cggctctcgt cttcccgcct cgcattcaac     120
gctcggctcg accaatcagc ggccgagttt tgcgctatga ccatataagg cgatacgttt     180
gtccgggtgg ggtgggacga gccattgcgg cttatcgcgc ggggagtac  cctctcaaaa     240
tgcactatgc actgccgtaa cactctttcg gaaagaatat ratacatcag tagatacctc     300
ttgaaaatta ggatccgatg cataccataa atcccaaat  tagagagaat aaaaggggtt     360
aattcgatcg agagtaatga cacttggaac gacctcccct ctggagaaag tcgacgatcc     420
gagaggtgga gtaagcgccc tactcactct ctcactcgca gtccaacccg agaggaagca     480
gcacgtacgc tcgtccgccc tttgtaagta tagcctccca ttcgtccaag ttctgcaaat     540
attcgtgctt taagaaccac cctagtacat tattaagccc cagtgagatc ccaatcgtga     600
cccaaaatac gtaatttagc tgtaattcgc ccaaacttcg ccctcacgaa cctaccggcg     660
ctcgcatggg ggtgtgtcct ggaccgtccc caagtgtctt gcttacttca atgcgaaagt     720
tttcctcggg ggtttatata ccgactcgaa agtcacttca aggcttgttt tacactcgcc     780
cgttgaagtt tccccggggt agtggaggcg aaacaggtgt tctcagaaag gtcctatttt     840
tagtccccga gttgctcccc aactgtcaag tccaactcca aaagtaatga ttttagtggt     900
atttgatggt attttccag  gctatttgtt ttattaagat tcttttcat  taattgggga     960
ttcgttgaat tttatatagt ccattttac  ttacgaagaa attgaaaatc cgattaatat    1020
gtgtaatgta agttaaatcg atcataataa tgtactaacg tgtaccacac tgctgaccgt    1080
ttttctctta aataggagat taagaaagca aacttggtcc ggagacagca tgtaggcgag    1140
agaaagggag ggagggaaa  ggagaggaaa gaggggggt  gggaggggta gggggagggg    1200
aagtgcgtgt tgccggtgac gtcacgcttg gcttcatata atgtcggttt aggatgtcga    1260
ggcttcagtc taacacgggt actcgctctg tgcacaacgt cattcgggcc ggtcccgcaa    1320
cgccatatag tcagtgactg tgatattaac tcggtaaata acgtgatttg agtctctaat    1380
atttttcccc ggattgtcgg gttttagtgt ggcacttgga tatcttttta atacttggtt    1440
caacgttatg gtggctttgg gggatcatag tgacacttcg tgatagtgtg gtggtgaatg    1500
aagctataca ataattgtga tttattggtg gattttctc  atgtggaaac actgttgtgg    1560
acatggatac gatttcttac ttgagtggct gtgcttaatc gcaactcttc cttccttaca    1620
gtagtaaaac aacaacaaca ag                                             1642
```

This β-actin promoter of the present invention is a constitutive, non-inducible, and non-developmentally regulated promoter. It is suitable for inducing constitutive expression of a transgene operably associated with the promoter molecule in an expression vector.

The present invention is also directed to nucleotide sequences having at least 90% similarity, at least 91% similarity, at least 92% similarity, at least 93% similarity, at least 94% similarity, at least 95% similarity, at least 96% similarity, at least 97% similarity, at least 98% similarity, and/or at least 99% similarity to SEQ ID NO:1.

The determination of percent identity, i.e. sequence similarity, between two nucleotide sequences can be accomplished using a mathematical algorithm. A preferred, non-limiting example of a mathematical algorithm utilized for the comparison of two sequences is the algorithm of Karlin et al., "Methods for Assessing the Statistical Significance of Molecular Sequence Features by Using General Scoring Schemes," *Proc. Natl. Acad. Sci.* 87:2264-2268 (1990), which is hereby incorporated by reference in its entirety, modified as in Karlin et al., "Applications and Statistics for Multiple High-Scoring Segments in Molecular Sequences," *Proc. Natl. Acad. Sci.* 90:5873-5877 (1993), which is hereby incorporated by reference in its entirety. Another non-limiting example of a mathematical algorithm utilized for the comparison of sequences is the algorithm of Myers et al., CABIOS (1989). Such an algorithm can be incorporated into the ALIGN program (version 2.0) which is part of the CGC sequence alignment software package. Additional algorithms for sequence analysis are known in the art and include ADVANCE and ADAM as described in Torellis et al. "ADVANCE and ADAM: Two Algorithms for the Analysis of Global Similarity between Homologous Informational Sequences," *Comput. Appl. Biosci.* 10:3-5 (1994), which is hereby incorporated by reference in its entirety, and FASTA described in Pearson et al., "Improved Tools for Biological Sequence Comparison," *Proc. Natl. Acad. Sci.* 85:2444-8 (1988), which is hereby incorporated by reference in its entirety.

In the shrimp, the β-actin promoter contains a complex array of cis-acting regulatory elements required for accurate and efficient initiation of transcription and for controlling expression of the β-actin gene. Transcripts of the shrimp β-actin gene are found in most of the major shrimp organs including the eyestalk, brain, heart, and hepatopancreas, suggesting that the shrimp β-actin is a cytoplasmic form of actin whose expression is constitutive, non-developmentally regulated, and non-inducible, and thus should remain constant throughout the lifespan of the shrimp.

Also encompassed by the present invention are fragments and variants of the above nucleic acid molecule. Fragments of the nucleic acid molecule of the present invention may be made, for example, synthetically, or by use of restriction enzyme digestion on an isolated nucleic acid molecule.

Another aspect of the present invention relates to a nucleic acid construct containing the shrimp nucleic acid promoter of the present invention. This involves incorporating the nucleic acid promoter molecule of the present invention into host cells using conventional recombinant DNA technology. Generally, this involves inserting the nucleic acid molecule into an expression vector to which the nucleic acid molecule is heterologous (i.e., not normally present). A vector is generally constructed to include a promoter, a nucleic acid molecule targeted for transcription and/or expression, and a 3' regulatory region having suitable transcriptional termination signals.

"Vector" is used herein to mean any genetic element, such as a plasmid, phage, transposon, cosmid, chromosome, virus, virion, etc., which is capable of replication when associated with the proper control elements, and which is capable of transferring gene sequences between cells. Thus, the term includes cloning and expression vectors, as well as viral vectors, including adenoviral and retroviral vectors.

Exemplary vectors include, without limitation, the following: lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC11, SV 40, pBluescript II SK +/- or KS +/- (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant genes may also be introduced into viruses, such as vaccinia virus. Recombinant viruses can be generated by transfection of plasmids into cells infected with virus.

Transcription of a target nucleic acid molecule in such a construct is dependent upon the presence of a promoter, which is a DNA sequence that directs the binding of RNA polymerase and thereby promotes mRNA synthesis. In this aspect of the present invention the promoter is the β-actin nucleic acid promoter molecule of the present invention having SEQ ID NO:1. The β-actin promoter of the present invention is a constitutive, non-inducible, non-developmental promoter. A constitutive promoter is a promoter that directs expression of a gene throughout the development and life of an organism. The promoter of the present invention is suitably, therefore, linked in the nucleic acid construct of the present invention to one or more nucleic acid molecules encoding a target protein or polypeptide of interest for which constitutive expression in the selected host is desired.

Any target nucleic acid molecule(s) of interest may be operably linked to this promoter molecule in a suitable vector, such that the nucleic acid molecule is under the control of the promoter of the present invention, including but not limited to, nucleic acids encoding viral proteins, such as coat proteins, growth regulating proteins, and proteins relating to enhanced stress tolerance in hosts transformed with such nucleic acid molecules, including heat shock proteins for increasing tolerance to cold-related stress.

Also present in the vector is a 3' regulatory region containing suitable transcription termination signals selected from among those which are capable of providing correct transcription termination and polyadenylation of mRNA for expression in the host cell of choice, operably linked to a nucleic acid molecule which encodes for a protein or polypeptide of choice. Exemplary 3' regulatory regions for the nucleic acid constructs of the present invention include, without limitation, the nopaline synthase ("nos") 3' regulatory region (Fraley, et al., "Expression of Bacterial Genes in Plant Cells," *Proc. Nat7. Acad. Sci. USA* 80(15):4803-4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," *Nature* 313(6005):810-812 (1985), which is hereby incorporated by reference in its entirety) and the 3' regulatory region of the shrimp β-actin gene included within the sequence in GenBank Accession Number AF300705. An example of a commonly-used 3' regulatory element for expression of genes of interest in animal cells is the SV40 polyadenylation signal derived from the SV40 virus. Virtually any 3' regulatory element known to be operable in the host cell of choice will suffice for proper expression of the genes contained in the plasmids of the present invention.

Also suitable in the nucleic acid construct of the present invention is a reporter gene (marker gene) such as β-galactosidase, luciferase, or green fluorescent protein (GFP) or enhanced green fluorescent protein (EGFP) gene of the bioluminescent jelly fish, *Aequorea Victoria* (Inoue, "Expression of Reporter Genes Introduced by Microinjection and Electroporation in Fish Embryos and Fry," *Mol. Mar. Biol. and Biotechnol.* 1(4/5): 266-270 (1992); Boulo et al., "Transient Expression of Luciferase Reporter Gene After Lipofection in Oyster (*Crassostrea gigas*) Primary Cell Cultures," *Mol. Mar. Biol. Biotechnol.* 5(3):167-74 (1996); Guillen et al., "Reporter Genes for Transgenic Fish Experiments," *Biotechnol. Apl.* 13(4):279-283 (1996); Arnone et al., "Green Fluorescent Protein in the Sea Urchin: New Experimental Approaches to Transcriptional Regulatory Analysis in Embryos and Larvae," *Development* 124(22):4649-4659 (1997); Husebye et al., "A Functional Study of the Salmon GnRH Promoter," *Mol. Mar. Biol. Biotechnol.* 6(4):357-363 (1997); Joore et al., "Regulation of the Zebrafish Goosecoid Promoter by Mesoderm Inducing Factors and Xwnt1," *Mech. Dev.* 55:3-18 (1997), which are hereby incorporated by reference in their entirety). A reporter gene is added to the nucleic acid construct of the present invention in order to evaluate the promoter's capacity to effectively direct expression of the target nucleic acid. Expression of the reporter gene is a good indication of whether the target gene was properly introduced into the host organism. The expression of the reporter gene also serves as a marker, helping to identify the organs and tissues in which the promoter is capable of driving target nucleic acid expression (Watson et al., "New Tools for Studying Gene Function," In: *Recombinant DNA*, New York: Scientific American Books, pp. 191-272 (1992); Winkler et al., "Analysis of Heterologous and Homologous Promoters and Enhancers in vitro and in vivo by Gene Transfer Into Japanese Medaka (*Oryzias latipes*) and Xiphophorus," *Mol. Mar. Biol. and Biotechnol.* 1 (4/5):326-337 (1992), which are hereby incorporated by reference in their entirety). Expression of the β-galactosidase gene can be monitored easily via spectrophotometry and expression of the EGFP gene can be visualized directly in live, transparent, transgenic shrimp under a fluorescence microscope (Amsterdam et al., "The *Aequorea Victoria* Green Fluorescent Protein Can be Used as a Reporter in Live Zebrafish Embryos," *Dev. Biol.* 171(1): 123-129 (1995); Kain et al., "Green Fluorescent Protein as a Reporter of Gene Expression and Protein Localization," *Biotechniques* 19(4):650-655 (1995); Burlage et al., "Green Fluorescent Protein in the Sea Urchin: New Experimental Approaches to Transcriptional Regulatory Analysis in Embryos and Larvae," *Development* 124(22):4649-4659 (1997); Hong et al., "Dynamics of Nontypical Apoptotic Morphological Changes Visualized by Green Fluorescent Protein in Living Cells with Infectious Pancreatic Necrosis Virus Infection," *J. Virol.* 73(6):5056-63 (1999), which are hereby incorporated by reference in their entirety) or handheld UV Lamp (Clare Chemical Research).

The promoter molecule of the present invention, a nucleic acid molecule encoding a protein or polypeptide of choice, a suitable 3' regulatory region and, if desired, a reporter gene, are incorporated into a vector-expression system of choice to prepare the nucleic acid construct of present invention using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety, and U.S. Pat. No. 4,237,224 to Cohen and Boyer, which is hereby incorporated by reference in its entirety, which describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

In one aspect of the present invention, a nucleic acid molecule encoding a protein of choice is inserted into a vector in the sense (i.e., 5'→3') direction, such that the open reading frame is properly oriented for the expression of the encoded protein under the control of the β-actin shrimp promoter of the present invention. Single or multiple nucleic acids may be ligated into an appropriate vector in this way, under the control of the promoter of the present invention.

In another aspect of the present invention, a target nucleic acid encoding a protein of choice is inserted into the vector in an antisense orientation (3'→5'). The use of antisense RNA to down-regulate the expression of specific plant genes is well known (van der Krol et al., "Antisense Genes in Plants: An Overview," *Gene* 72:45-50 (1988); van der Krol et al., "Inhibition of Flower Pigmentation by Antisense CHS Genes: Promoter and Minimal Sequence Requirements for the Antisense Effect," *Plant Mol. Biol.* 14(4):457-66 (1990); Mol et al., "Regulation of Plant Gene Expression by Antisense RNA," *FEBS Lett.* 286:427-430 (1990); and Smith et al., "Antisense RNA Inhibition of Polygalacturonase Gene Expression in Transgenic Tomatoes," *Nature* 334:724-726 (1988); which are hereby incorporated by reference in their entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). Antisense methodology takes advantage of the fact that nucleic acids tend to pair with "complementary" sequences. By complementary, it is meant that polynucleotides are capable of base-pairing according to the standard Watson-Crick rules. In the target cell, the antisense nucleic acids hybridize to a target nucleic acid and interfere with transcription, and/or RNA processing, transport, translation, and/or stability. The overall effect of such interference with the target nucleic acid function is the disruption of protein expression.

Accordingly, both antisense and sense forms of nucleic acids are suitable for use in the nucleic acid constructs of the invention. A single construct may contain both sense and antisense forms of one or more desired nucleic acids encoding a protein.

Alternatively, the nucleic acid construct of the present invention may be configured so that the DNA molecule encodes an mRNA which is not translatable, i.e., does not result in the production of a protein or polypeptide. This is achieved, for example, by introducing into the desired nucleic acid sequence of the present invention one or more premature stop codons, adding one or more bases (except multiples of 3 bases) to displace the reading frame, and removing the translation initiation codon (U.S. Pat. No. 5,583,021 to Dougherty et al., which is hereby incorporated by reference in its entirety). This can involve the use of a primer to which a stop codon, such as TAA, TAG, or TGA, is inserted into the sense (or "forward") PCR-primer for amplification of the full nucleic acid, between the 5' end of that primer, which corresponds to the appropriate restriction enzyme site of the vector into which the nucleic acid is to be inserted, and the 3' end of the primer, which corresponds to the 5' sequence of the enzyme-encoding nucleic acid. Genes can be effective as silencers in the non-translatable antisense forms, as well as in the non-translatable sense form (Baulcombe, "Mechanisms of Pathogen-Derived Resistance to Viruses in Transgenic Plants," *Plant Cell* 8:1833-44 (1996); Dougherty et al., "Transgenes and Gene Suppression: Telling us Something New?" *Current Opinion in Cell Biology* 7:399-05 (1995); Lomonossoff, "Pathogen-Derived Resistance to Plant Viruses," *Ann. Rev. Phytopathol.* 33:323-43 (1995), which are hereby incorporated by reference in their entirety).

Once the nucleic acid construct of the present invention has been prepared, it is ready to be incorporated into a host cell. Accordingly, another aspect of the present invention relates to a recombinant cell, or "host" cell containing a nucleic acid construct of the present invention. A variety of vector-host systems known in the art may be utilized to express the protein-encoding sequence(s). Primarily, the vector system must be compatible with the host cell used. Host-vector systems include, but are not limited to, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and animal cells, including marine fish, crustacean, particularly shrimp, and other marine animals, infected by bacterial vector. Host cells are prepared by delivery of vector into the host organism.

Three common methods of vector-expression for foreign nucleic acid delivery are electroporation (Muller et al., "Introducing Foreign Genes Into Fish Eggs With Electroporated Sperm as a Carrier," *Mol. Mar. Biol. Biotechnol.* 1:276-281 (1992); Powers et al., "Electroporation: a Method for Transferring Genes Into the Gametes of Zebra Fish (*Brachydanio rerio*), Channel Catfish (*Ictalurus punctatus*), and Common Carp (*Cyprimus carpio*)," *Mol. Mar. Biol. Biotechnol.* 1:301-308 (1992); Sin et al., "Gene Transfer in Chinook Salmon by Electroporating Sperm in the Presence of PRSV-lacZ DNA," *Aquaculture* 117:57-69 (1993); Powers et al., "Electroporation as an Effective Means of Introducing DNA Into Abalone (*Haliotis rufescens*) Embryos," *Mol. Mar. Biol. Biotechnol.* 4(4):369-375 (1995); Tsai et al., "Sperm as a Carrier to Introduce an Exogenous DNA Fragment Into the Oocyte of Japanese Abalone (*Haliotis divorsicolor suportexta*)," *Transgenic Res.* 6(1):85-95 (1997); Fraga et al., "Introducing Antisense Oligonucleotides into Paramecium via Electroporation," *J. Eukaryot. Microbiol.* 45(6):582-8 (1998); Preston et al., "Delivery of DNA to Early Embryos of the Kuruma Prawn, *Penaeus japonicus*," *Aquaculture* 181:225-234 (2000), which are hereby incorporated by reference in their entirety), ballistic bombardment (Zelenin et al., "The Delivery of Foreign Genes Into Fertilized Eggs Using High-Velocity Microprojectiles," *FEBS Lett.* 287(1-2):118-120 (1991); Akasaka et al., "Introduction of DNA Into Sea Urchin Eggs by Particle Gun," *Mol. Mar. Biol. Biotechnol.* 4(3):255-261 (1995); Gendreau et al., "Transient Expression of a Luciferase Reporter Gene After Ballistic Introduction Into *Artemia Franciscana* (Crustacea) Embryos," *Aquaculture* 133:199-205 (1995); Baum et al., "Improved Ballistic Transient Transformation Conditions for Tomato Fruit Allow Identification of Organ-Specific Contributions of I-Box and G-Box to the RBCS2 Promoter Activity," *Plant J.* 12(2):463-9 (1997); Udvardi et al., "Uptake of Exogenous DNA Via the Skin," *J. Mol. Med.* 77(10):744-50 (1999), which are hereby incorporated by reference in their entirety) and microinjection (Udvardi et al., "Uptake of Exogenous DNA Via the Skin," *J. Mol. Med.* 77(10):744-50 (1999); Penman et al., "Patterns of Transgene Inheritance in Rainbow Trout (*Oncorhynchus Mykiss*)," *Mol. Reprod. Dev.* 30:201-206 (1991); Damen et al., "Transcriptional Regulation of Tubulin Gene Expression in Differentiating Trochoblasts During Early Development of *Patella Vulgata*," *Development* 120:2835-2845 (1994); Gaiano et al., "Highly Efficient Germ-Line Transmission of Proviral Insertions," *Proc. Natl. Acad. Sci. USA* 93:7777-7782 (1996); Cadoret et al., "Microinjection of Bivalve Eggs: Application in Genetics," *Mol. Mar. Biol. Biotechnol.* 6(1): 7277 (1997); Li et al., "Transfer of Foreign Gene to Giant Freshwater Prawn (*Macrobrachium rosenbergii*) by Spermatophore-Microinjection," *Mol. Reprod. Dev.* 56(2):149-54 (2000), which are hereby incorporated by reference in their entirety). Among these three methods, microinjection is considered to be the most tedious, but most efficient, method for transferring foreign nucleic acid into marine and fresh water species. It allows precision in delivery of exogenous nucleic acid and increases the chances that a treated egg will be transformed. The introduced nucleic acid is ultimately integrated into the chromosomes of the microinjected organism. Preston et al., "Delivery of DNA to Early Embryos of the Kuruma Prawn, *Penaeus japonicus*," *Aquaculture* 181:225-234 (2000) (which is hereby incorporated by reference in its entirety), examined the relative efficiency of microinjection, electroporation, and particle bombardment for introducing nucleic acid into the embryos of the Kuruma prawn, *Litopenaeus japonicus*, and found that microinjection is the most reliable technique but very time consuming. Electroporation is a desirable method for large scale gene transfer. However, if the host mortality is high, an alternative non-surgical technique (e.g., spermatophore-microinjection) can be used as the delivery system. While stable expression is generally preferable, transient expression is suitable for some uses of the nucleic acid constructs of the present invention. Therefore, the choice of delivery system may vary depending on the type of expression desired.

After transformation, the transformed host cells can be selected and expanded in suitable culture. Preferably, transformed cells are first identified using a selection marker simultaneously introduced into the host cells along with the nucleic acid construct of the present invention. Suitable markers include those genes described above as reporter genes, i.e., β-glucuronidase, luciferase, EGFP, or markers encoding for antibiotic resistance, such as the nptII gene which confers kanamycin resistance (Fraley et al., "Expression of Bacterial Genes in Plant Cells," *Proc. Nat'l Acad. Sci. USA* 80(15): 4803-4807 (1983), which is hereby incorporated by reference in its entirety), or gentamycin, G418, ampicillin, streptomycin, spectinomycin, tetracycline, chloramphenicol, and the like. A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics or biosynthesis selection markers are preferred.

The present invention also relates to a transgenic animal transformed with a nucleic acid construct of the present invention described above having a nucleic acid molecule encoding a protein under the control of the β-actin promoter of the present invention. This involves preparing a nucleic acid construct as described above containing the β-actin promoter, a nucleic acid molecule encoding a desired protein, and a 3' regulatory region for termination; incorporating the nucleic acid construct into a suitable vector-host system; and transforming an animal using a suitable delivery system, such as those described above. Animals suitable for this aspect of the present invention include, without limitation, marine fish; crustaceans, including shrimp and prawns; shellfish; and insects.

When stable transformation of a transgenic animal is achieved, the gene is incorporated into the organism's genome, and the gene is, therefore, heritable. Accordingly, the present invention also relates to the progeny of the transgenic animal transformed with the nucleic acid construct described above having a nucleic acid molecule encoding a protein under the control of the β-actin promoter of the present invention, wherein the progeny harbors the transformed nucleic acid.

Another aspect of the present invention is directed to a nucleic acid expression cassette including a β-actin promoter molecule isolated from shrimp having SEQ ID NO:1, a multiple cloning site, an operable termination segment, and a nucleic acid molecule encoding a detectable marker. In this aspect, a nucleic acid expression cassette is prepared generally as described for the making of the nucleic acid construct having the β-actin promoter of the present invention, with the promoter molecule and a suitable 3' termination segment (meaning a polyadenylation signal and a termination signal). However, the promoter is incorporated into a vector having a multiple cloning site (MCS) for the insertion of one or more nucleic acid molecules of choice by a user. In one embodiment, the expression cassette also contains a detectable marker. Exemplary markers are described supra. The promoter molecule, a suitable 3' termination segment and, if desired, a detectable marker, are ligated into a vector having a MCS using standard cloning procedures known in the art, such as described by Sambrook et al., *Molecular Cloning: A Laboratory Manual*, Third Edition, Cold Spring Harbor: Cold Spring Harbor Laboratory Press, New York (2001) and U.S. Pat. No. 4,237,224 to Cohen and Boyer, which are hereby incorporated by reference in their entirety.

The present invention also relates to a method of imparting to an animal resistance against a pathogen. This involves transforming an animal with the nucleic acid construct of the present invention described above having the β-actin promoter of the present invention, a nucleic acid molecule encoding a protein for resistance to a pathogen, and an operable 3' regulatory region. In one aspect of the present invention, the pathogen is a virus. Exemplary viruses against which resistance is imparted include, without limitation, white spot syndrome virus ("WSSV"), yellow head virus ("YHV"), Taura syndrome virus ("TSV"), and infectious hypodermal and hematopoietic necrosis virus ("IHHNV"). In one embodiment of the present invention, the nucleic acid molecule encodes a viral coat protein, or a fragment thereof. Suitable nucleic acid molecules are those encoding for the viral coat protein or polypeptide of (WSSV), (YHV), (TSV), and (IHHNV). One or more coat protein-encoding nucleic acid molecules can be used in a single construct so as to confer resistance to multiple viruses to one animal with a single vector.

While not wishing to be bound by theory, by use of the constructs of the present invention, it is believed that viral resistant transgenic animals can result using RNA-mediated post-transcriptional gene silencing. The strategy is to introduce a transgene consisting of sense and/or antisense versions of target gene (for example, TSV coat protein and the IHHNV coat protein) fragments into a host animal, so that the expressed RNA transcripts will interfere with the translation process of the TSV and IHHNV coat protein genes, thereby inhibiting viral replication in the animal.

More particularly, the silencer DNA molecule is believed to boost the level of heterologous RNA within the cell above a threshold level. This activates the degradation mechanism by which viral resistance is achieved.

Posttranscriptional gene silencing (PTGS) based on RNA interference (RNAi) destroys RNA in a sequence-specific manner (Baulcombe, "RNA Silencing," *Curr. Biol.* 12(3): R82-4 (2002); Hutvagner et al., "RNAi: Nature Abhors a Double-Strand," *Curr. Opin. Genet. Dev.* 12(2):225-232 (2002), Hutvagner et al., "A MicroRNA in a Multiple-Turnover RNAi Enzyme Complex," *Science* 297(5589):2056-2060 (2002), which are hereby incorporated by reference in their entirety) and functions in the natural immunity of animal cells. Significant progress in the area of viral resistance through RNA-mediated gene silencing has been achieved through research of RNAi in plants (Waterhouse et al., "Virus Resistance and Gene Silencing in Plants Can be Induced by Simultaneous Expression of Sense and Antisense RNA," *Proc. Natl. Acad. Sci. USA* 95(23):13959-64 (1998); Pang et al., "Resistance to Squash Mosaic Comovirus in Transgenic Squash Plants Expressing its Coat Protein Genes," *Mol. Breed.* 6:87-93 (2000); Vance et al., "RNA Silencing in Plants—Defense and Counterdefense," *Science* 292(5525): 2277-2280 (2001); Hongwei et al., "Induction and Suppression of RNA Silencing by Animal Virus," *Science* 296:1319-1321 (2002), which are hereby incorporated by reference in their entirety) and animals (Takayama et al., "Antisense RNA-Mediated Inhibition of Viral Infection in Tissue Culture and Transgenic Mice," In: Molecular Biology of RNA, Less (ed.), pp. 299-310. New York (1989); Kim et al., "Examination of Antisense RNA and Oligodeoxynucleotides as Potential Inhibitors of Avian Leukosis Virus Replication in RP30 Cells," *Poultry Sci.* 77:1400-10 (1998); Player et al., "Potent Inhibition of Respiratory Syncytial Virus Replication Using a 2-5A-Antisense Chimera targeted to Signals Within the Virus Genomic RNA," *Proc. Natl. Acad. Sci. USA* 95:8874-9 (1998); Knight et al., "A Role for the RNase III Enzyme DCR-1 in RNA Interference and Germ Line Development in Caenorhabditis Elegans," *Science* 293(5538):2269-2271 (2001); Tang et al., "Detection and Quantification of Infectious Hypodermal and Hematopoietic Necrosis Virus in Penaeid Shrimp by Real-Time PCR," *Dis. Aquat. Org.* 44(2): 79-85 (2001); Korneev et al., "Suppression of Nitric Oxide (NO)-Dependent Behavior by Double-Stranded RNA-Mediated Silencing of a Neuronal NO Synthase Gene," *J. Neurosci.* 22(11):RC227 (2002); Gitlin et al., "Short Interfering RNA Confers Intracellular Antiviral Immunity in Human Cells," *Nature*, Online publication (2002), which are hereby incorporated by reference in their entirety). Current review of RNA-mediated gene silencing mechanisms have been extensively described (Ahlquist, "RNA-Dependent RNA Polymerases, Viruses, and RNA Silencing," *Science* 296:1270-1273 (2002), which is hereby incorporated by reference in its entirety). Examples of transgenic animals include: inhibition of Moloney murine leukemia virus in mice with anti-sense RNA against the retroviral packaging sequences (Han et al., "Inhibition of Moloney Murine Leukemia Virus-Induced Leukemia in Transgenic Mice Expressing Antisense RNA Complementary to the Retroviral Packaging Sequences," *Proc. Natl. Acad. Sci. USA* 88:4313-17 (1991), which is hereby incorporated by reference in its entirety), transgenic mice resistant to hepatitis virus (Sasaki et al., "Transgenic Mice With Antisense RNA Against the Nucleocapsid Protein mRNA of Mouse Hepatitis Virus," *J. Vet. Med. Sci.* 55(4):549-54 (1993), which is hereby incorporated by reference in its entirety), and *Aedes aegypti* mosquitoes resistant to luciferase expression (Johnson et al., "Inhibition of Luciferase Expression in Transgenic *Aedes Aegypti* Mosquitoes by Sindbis Virus Expression of Antisense Luciferase RNA," *Proc. Natl. Acad. Sci. USA* 96(23): 13399-403 (1999), which is hereby incorporated by reference in its entirety). Generally, pathogen resistance was mediated through production of viral coat protein RNA in the above listed studies. Viral coat protein genes, and fragments thereof, have been used successfully in plants for RNA-mediated pathogen-derived resistance since presumably, the transcript is highly expressed and is very stable (Pang et al., "Nontarget DNA Sequences Reduce the Transgene Length Necessary for RNA-Mediated Tospovirus Resistance in Transgenic Plants," *Proc. Natl. Acad. Sci. USA* 94:8261-8266 (1997), which is hereby incorporated by reference in its entirety). It was demonstrated that only a portion of the coat protein gene was required to confer resistance against the viral pathogen. For example, a minimum length (somewhere between 236-387 bp) of the gene for the 29 Kd nucleocapsid protein of tomato spotted wilt virus ("TSWV") was required to develop RNA-mediated resistance in transgenic *Nicotiana benthamiana* plants (Pang et al., "Nontarget DNA Sequences Reduce the Transgene Length Necessary for RNA-Mediated Tospovirus Resistance in Transgenic Plants," *Proc. Natl. Acad. Sci. USA* 94:8261-8266 (1997), which is hereby incorporated by reference in its entirety). It was also determined that any region of the coding sequence for the TSWV nucleocapsid protein can be used to develop virus resistance (Pang et al., "Nontarget DNA Sequences Reduce the Transgene Length Necessary for RNA-Mediated Tospovirus Resistance in Transgenic Plants," *Proc. Natl. Acad. Sci. USA* 94:8261-8266 (1997), which is hereby incorporated by reference in its entirety).

Animals suitable for this aspect of the present invention include, without limitation, those selected from the group consisting of marine fish, crustaceans (including prawns and shrimp), shellfish, and insects.

The present invention also relates to a method of regulating the growth of an animal. This involves transforming an animal with a nucleic acid construct of the present invention having the β-actin promoter of the present invention operably linked to a nucleic acid molecule encoding a growth regulating protein, and a 3' regulatory region. Nucleic acid molecules suitable for this aspect of the present invention include those that encode proteins that up-regulate growth and down-regulate growth. Examples of suitable proteins that can be used to up-regulate growth include growth hormones including, without limitation, the androgenic hormone. Animals suitable for this aspect of the present invention include, without limitation, those selected from the group consisting of marine fish, crustaceans (including prawns and shrimp), shellfish, and insects.

Another aspect of the present invention is directed to a method of increasing stress tolerance in an animal, including stress induced by cold. This involves transforming an animal with the nucleic acid construct of the present invention having the β-actin promoter of the present invention operably linked to a nucleic acid molecule encoding protein and a 3' regulatory region. Nucleic acid molecules suitable for this aspect of the present invention include those encoding for a protein that increases stress tolerance in an animal. An exemplary protein would be a heat shock protein, such as HSP70 or HSP26, which may enhance cold tolerance in an animal. Animals suitable for this aspect of the present invention include without limitation, those selected from the group consisting of marine fish, crustaceans (including prawns and shrimp), shellfish, and insects.

EXAMPLES

The Examples set forth below are for illustrative purposes only and are not intended to limit, in any way, the scope of the present invention.

Example 1

Methods and Procedures for Isolation and Identification of Shrimp β-Actin Promoter Nucleic Acid Sequence and Associated Transcriptional Regulatory Elements DNA Extraction To obtain Shrimp DNA, the muscle tissue of one *Litopenaeus vannamei*, frozen at −80° C., was ground with a precooled mortar and pestle and lysed in a Proteinase K solution. DNA from the lysate was then extracted with Phenol/Chloroform and used as a template for PCR.

Beta-Actin Intron 1 Sequence and Promoter Sequence: PCR and Sequencing

Oligonucleotide primer pairs for PCR were designed using NetPrimer (Premier Biosoft International), based on the GenBank mRNA sequence submission AF300705.1. Part of the first intron sequence was obtained by using the primers:

LV-B-act-27-Se: 5'-GAGCCCGAGAGGAAGCAG-3' (SEQ ID NO:2) and
LV-B-act-663-As: 5'-CTTCATCAGGTAGTCTGTGAGGTC-3' (SEQ ID NO:3)) to generate PCR products that were then gel-purified using QiaQuick Gel-Extraction Kit (Qiagen) and sequenced with the automatic sequencing method using DyeDeoxy Terminator chemistry (Applied Biosystems) (FIG. 1). The intron sequence was used to design a set of nested primers for inverse PCR: Outer iPCR Primers:

iPCR out il Se: 5'-ATTCGCCTAAACTCCGCCCTCACG-3' (SEQ ID NO:4) and
iPCR out il As: 5'-TATTTTGGGTCACGATTGGGGTCTCAC-3' (SEQ ID NO:5) were designed to generate a PCR product from a self-ligated, circularized genomic fragment produced by a N1a III restriction enzyme digestion and followed by a ligation of highly diluted concentrations of the restriction enzyme digestion generated fragments. Inner (nested) Primers:

iPCR inr Nil Se: 5'-CGCCCTCACGAACCTACCG-3' (SEQ ID NO:6) and
iPCR inr Nil As: 5'-AGAACTTGGACGAATGGGAGGCTA-3' (SEQ ID NO:7) were used to generate a slightly smaller nested PCR product, using a gel-purified PCR product from the previous PCR as a template to obtain a high concentration of gel-purified PCR product, which was used as a template for automatic Sanger sequencing with DyeDeoxy Terminators and the aforementioned primers.

Restriction Enzyme Digest

An NlaIII restriction enzyme digest was set up using 0.75 µl of NlaIII enzyme (at a concentration of 15 U/µl), 5 µl of NEB Buffer 4 (10×), and 6 µl of Shrimp DNA (from the phenol/chloroform preparation, at a concentration of 170 ng/µl) in a final reaction volume of 50 µl. DNA was digested for 2 hours at 37° C., followed by heat inactivation at 65° C. for 20 minutes.

Self-Ligation Reaction

The resulting fragmented DNA (1 µg) was used in a self-ligation reaction at 16° C. for 24 hours with 50 Weiss units of T4 DNA Ligase in 1× Ligation Buffer (NEB) in a total volume of 1 ml. 500 µl of the ligation reaction was ethanol-precipitated by adding 50 µl of 3M Sodium Acetate (pH 5.2) and 1 ml of 100% ethanol, followed by vortexing and centrifugation at 18,000 g for 10 minutes, and then by decanting the supernatant and washing with 1 ml 70% ethanol, with another vortexing and centrifugation at 18,000 g for 10 minutes. The pellet was air-dried and resuspended in 50 µl of water for a final concentration of 10 ng/µl.

Inverse PCR

Figure 2:
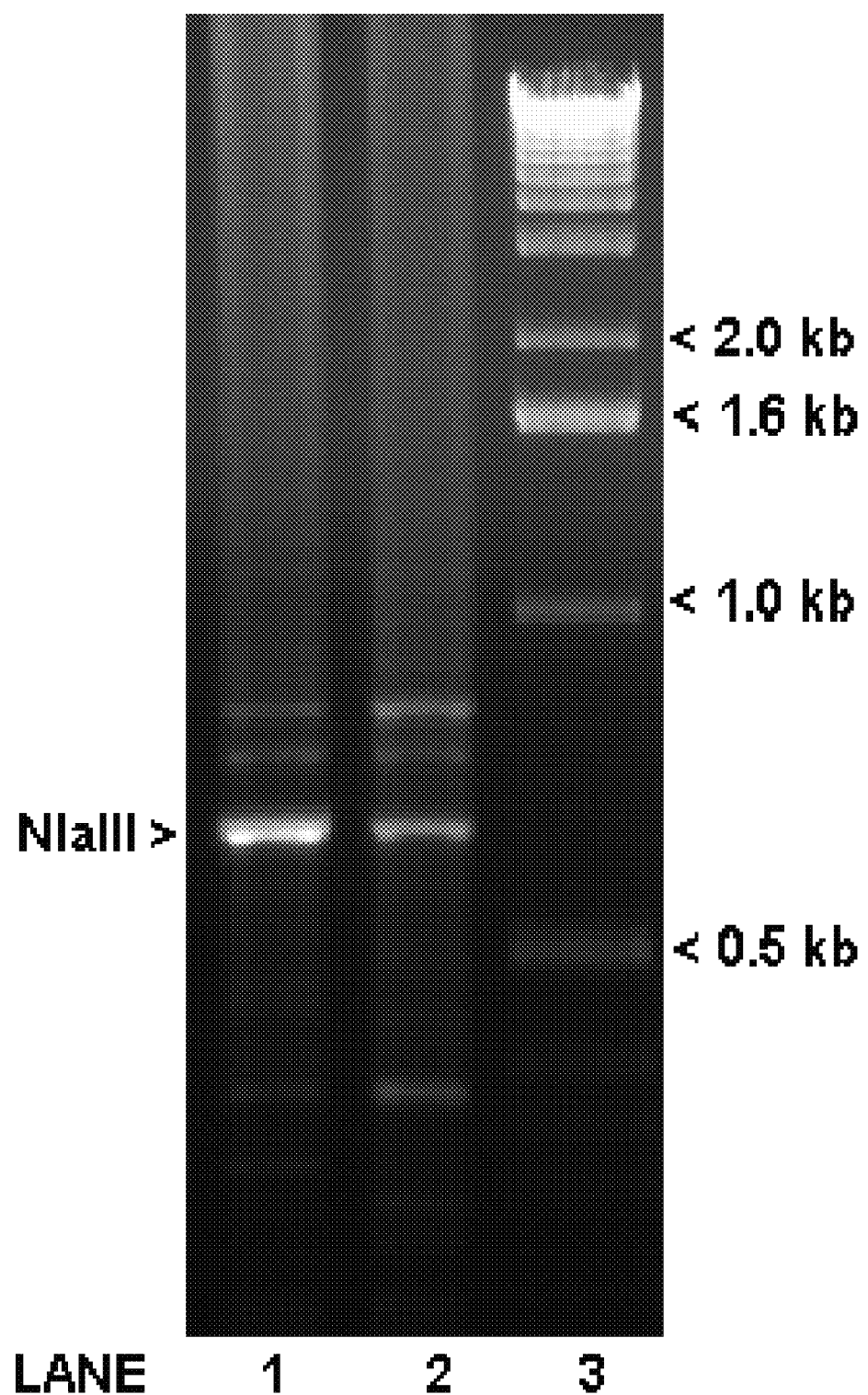
FIG. 2 is an electrophoresis image. Lane 1: Invitrogen 1 kb DNA Ladder molecular size standard. Lanes 2 and 3: Inverse PCR products generated using self-circularized (self-ligated) NlaIII restriction enzyme digested Pacific White Shrimp genomic DNA as a template for these primers: iPCR out il Se (SEQ ID NO:4) and iPCR out il As (SEQ ID NO:5).
Figure 3:
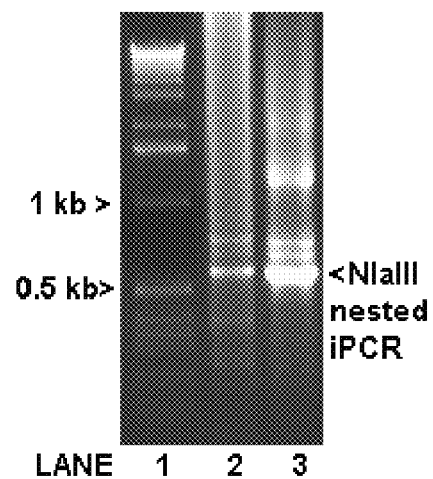
FIG. 3 is an electrophoresis image. Lane 1: Invitrogen 1 kb DNA Ladder molecular size standard. Lanes 2 and 3: Nested Inverse PCR products generated using the PCR products from the first inverse PCR (FIG. 2) as a template for these primers: iPCR inr Nil Se (SEQ ID NO:6) and iPCR inr Nil As (SEQ ID NO:7).

The self-ligated DNA was used as a template (4 µl in a 25 µl reaction) for inverse PCR using the primers iPCR out il Se (SEQ ID NO:4) and iPCR out il As (SEQ ID NO:5). Reaction conditions were: initial 3 minute denaturation at 95° C., followed by 37 cycles at 95° C. for 1 min, 30 seconds at 50° C., 10 minutes at 72° C., with a 20 minute final extension at 72° C. (FIG. 2). 5 µl of the resulting PCR reaction products were used as a template for nested iPCR using the primers iPCR inr Nil Se (SEQ ID NO:6) and iPCR inr Nil As (SEQ ID NO:7) with the following PCR conditions: initial 3 minute denaturation at 95° C., followed by 37 cycles at 95° C. for 1 min, 30 seconds at 54° C., 4 minutes at 72° C., with a 10 minute final extension at 72° C. (FIG. 3). The resulting product was gel purified using a QiaQuick Gel-Extraction Kit (Qiagen) and sequenced with the automatic Sanger sequencing method using DyeDeoxy Terminator chemistry (Applied Biosystems) using the aforementioned primers. The resulting sequence contained the promoter region sequence and the 5'

UTR sequence, as well as the 1st intron sequence of the Shrimp beta-actin gene. This sequence was used to design a set of primers for generating a PCR product containing the entire 1st intron, the promoter region sequence, and the entire 5' UTR sequence up to, but not including, the start codon (ATG), as well as three similar, shorter products.

Intron Sequence Gap Completion

Figure 4:
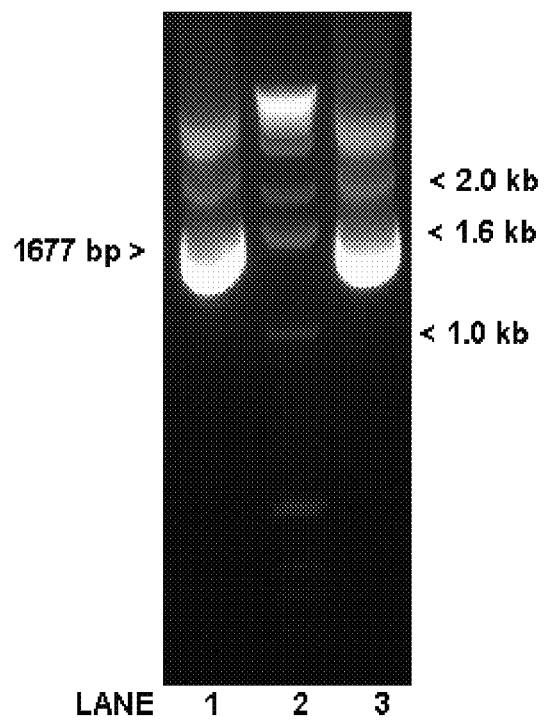
FIG. 4 is an electrophoresis image. Lanes 1 and 3: PCR products generated using primers Fsbp-1 (SEQ ID NO:8) and LV Bact Met-1 As (SEQ ID NO:9). Lane 2: Invitrogen 1 kb DNA Ladder molecular size standard.

The remaining sequence of intron 1 was obtained by generating a PCR fragment containing the entire intron 1, the promoter region sequence, and the entire 5' UTR sequence up to, but not including, the start codon (ATG) using the primers:
Fsbp-1: 5'-AAAATGAGGCGGCGGCAATGAT-3' (SEQ ID NO:8) and
LV Bact Met-1 As: 5'-CTTGTTGTTGTTGTTTTACTACT-GTAAGGAAG GAAG-3' (SEQ ID NO:9).
Reaction conditions were: initial 3 minute denaturation at 95° C., followed by 35 cycles at 95° C. for 30 seconds, 30 seconds at 58° C., 3 minutes at 72° C., with a 10 minute final extension at 72° C. (FIG. 4). The PCR product was gel purified, as described above, cloned into a pCR2.1 TOPO vector (Invitrogen) and used as a template for automatic Sanger sequencing with DyeDeoxy Terminators and
M13 F: 5'-GTAAAACGACGGCCAG-3' (SEQ ID NO:15),
M13 R: 5'-CAGGAAACAGCTATGAC-3' (SEQ ID NO:16), and iPCR out il Se (SEQ ID NO:4) SEQUENCING primers. The template used in the aforementioned PCR was a pCR2.1 TOPO vector clone that was generated as described above, with the difference being that in generating the insert, Shrimp genomic DNA was used as a template with primers:
Rsbp-1: 5'-TACAACCAGGGCGGCTACTTCGTC-3' (SEQ ID NO:17) and
Fsbp-1 (SEQ ID NO:8).

Evaluation of the Comparative Level of Shrimp Beta-Actin Promoter-Driven Expression of a Transgene The pCR2.1 TOPO vector clone containing the insert generated with primers Fsbp-1 (SEQ ID NO:8) and LV Bact Met-1 As (SEQ ID NO:9) was used to subclone the insert into an expression vector from which the CMV promoter and beta-globin intron had been removed. This clone was evaluated for the comparative level of Shrimp Beta-actin promoter-driven expression of a transgene. This process was also performed with another construct containing a PCR fragment generated with primers:
Fsbp-1 (SEQ ID NO:8) and
LV BA ilJ: 5'-ATACTTGGAAAGGGCGGACGAGCG-3' (SEQ ID NO:10), which contained some, but not all of the intron 1 sequence (with the intron splice site recognition sequence altered by changing the corresponding bases within the primer LV BA ilJ (SEQ ID NO:10)), the promoter region sequence, and the 5' UTR sequence up to the intron 1 junction. It was, however, necessary to include all of the intron 1 sequence in order to obtain a higher level of expression, which was the reason for creating the new insert with primers: Fsbp-1 (SEQ ID NO:8) and LV Bact Met-1 As (SEQ ID NO:9).

Descriptions of the Clones Containing the *Litopenaeus vannamei* Beta-Actin Promoter "Complete"—Contains promoter region, the complete 5' UTR, and the complete intron 1 interrupting the 5' UTR. Does not contain the initiation of translation ATG ("Met") codon and ends at the nucleotide preceding it. PCR fragments were generated with primers: Fsbp-1 (SEQ ID NO:8) and LV Bact Met-1 As (SEQ ID NO:9).

"Native"—Contains promoter region, 2 native PyRIMs, and the sequence up to intron 1, including several bases of the intron sequence (derived from the reverse primer) with the intron splicing site recognition sequence "GT" substituted by synthetic "CC" to prevent splicing. PCR fragments were generated with primers:
Fsbp-1 (SEQ ID NO:8) and LV BA ilJ (SEQ ID NO:10).

"39S"—Contains promoter region and 1 native PyRIM "CTCACTCT" repeated four times. PCR fragments were generated with primers:
Fsbp-1 (SEQ ID NO:8) and
LV BA PyRIM39S: 5'-AGAGTGAGAGAGTGAGAGAGT-GAGAGAGTGAGTAGGGCG-3' (SEQ ID NO:13).

"55S"—Contains promoter region and 1 native PyRIM "CTCACTCT" repeated six times. The insert (promoter region) is in reverse orientation in the pCR2.1 "TA" vector in comparison to "Native" and "39S". The inserts can be subcloned by removal of the insert from the clones with EcoRI, which cuts both sides around the insert, not within it. PCR fragments were generated with primers:
Fsbp-1 (SEQ ID NO:8) and
LV BA PyRIM55S: 5'-AGAGTGAGAGAGTGAGAGAGT-GAGAGAGTGAGAG AGTGAGAGAGTGAG-TAGGGCG-3' (SEQ ID NO:14).

PCR fragments were also generated with primers:
Fsbp-1 (SEQ ID NO:8) and
LV BA PyRIM: 5'-ACTGCGAGTGAGAGAGTGAG-TAGGGCG-3' (SEQ ID NO: 11) or
LV BA PyRIM34: 5'-GGGTTGGACTGCGAGT-GAGAGAGTGAGTAGGGCG-3' (SEQ ID NO:12).

Figure 5:
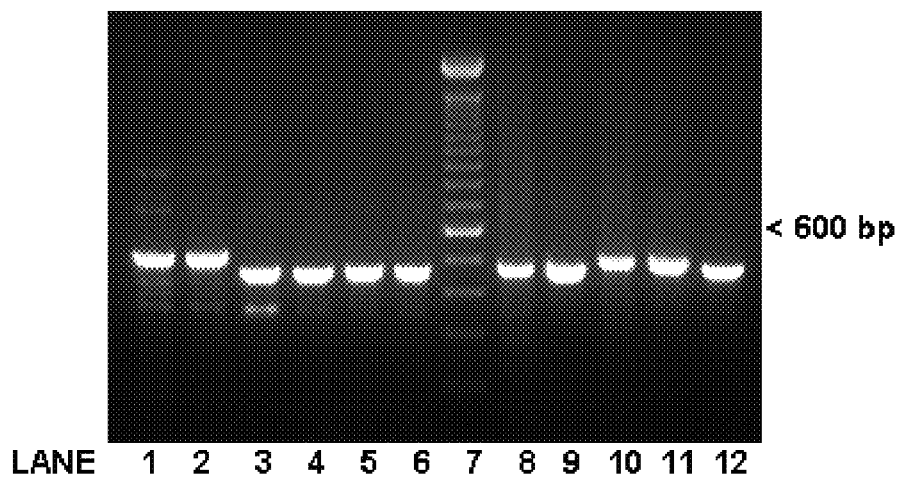
FIG. 5 is an electrophoresis image. Lanes 1 and 2: 511 bp PCR products used to create clone "Native." Lanes 3 and 4: 462 bp PCR products. Lanes 5 and 6: 469 bp PCR products. Lane 7: Invitrogen 100 bb DNA Ladder molecular size standard. Lanes 8 and 9: 474 bp PCR products used to create clone "39S." Lanes 10 and 11: 491 bp PCR products used to create clone "55S." Lane 12: 469 bp PCR product. All products were generated using Pacific White Shrimp genomic DNA as a template for these primers: Lanes 1 and 2: Fsbp-1 (SEQ ID NO:8) and LV BA ilJ (SEQ ID NO:10). Lanes 3 and 4: Fsbp-1 (SEQ ID NO:8) and LV BA PyRIM (SEQ ID NO:11). Lanes 5, 6, and 12: Fsbp-1 (SEQ ID NO:8) and LV BA PyRIM34 (SEQ ID NO:12). Lanes 8 and 9: Fsbp-1 (SEQ ID NO:8) and LV BA PyRIM39S (SEQ ID NO:13). Lanes 10 and 11: Fsbp-1 (SEQ ID NO:8) and LV BA PyRIM55S (SEQ ID NO:14). All even-numbered lanes had an annealing temperature of 59° C. and all odd-numbered lanes had an annealing temperature of 54° C. during the PCR.
Figure 6:
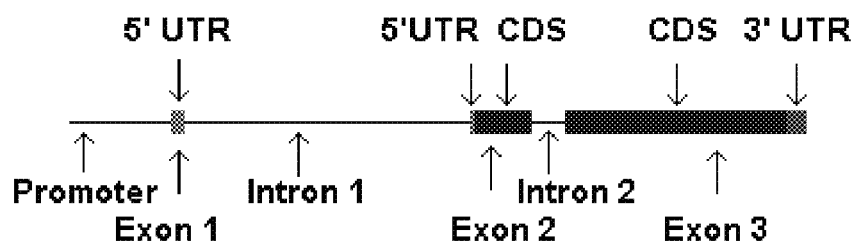
FIG. 6 is a schematic diagram of the *Litopenaeus vannamei* beta-actin gene. In the diagram, the promoter region and associated transcriptional regulatory elements located within the sequence of the 1st intron cover approximately half of the entire sequence depicted.

However, these two PCR fragments were not cloned into pCR2.1 vector. The PCR products produced with the other primer sets were cloned into pCR2.1 vectors and subsequently subcloned into an expression vector from which the CMV promoter and beta-globin intron had been removed. The PCR conditions were: initial 5 minute denaturation at 95° C., followed by 35 cycles at 95° C. for 30 seconds, 20 seconds at 54 or 59° C., 1 minute at 72° C., with a 5 minute final extension at 72° C. (FIG. 5).

Example 2

Shrimp β-Actin Promoter and Associate Transcriptional Elements Plasmid Construction Construct pAAV-CMV-mRFP using CMV as the promoter for RFP gene expression was employed as a positive control for the transfection test (FIG. 7). A promoterless pAAV-mRFP was also included in this study as a negative control.

To test and determine the biological activity of the putative shrimp promoter, the CMV promoter was removed from pAAV-mRFP by Mlu I and Sac II digestion. The shrimp M-actin promoter DNA fragment and associated transcriptional regulatory elements were released from plasmid pβ-actin-GFP (pGFP-1) by Hind III and Sac II digestion, and subsequently cloned into the digested pAAV-mRFP DNA to generate pAAV-β-actin-P-mRFP construct (FIG. 7).

Plasmid DNA was extracted from the identified colonies following standard transformation and used to transfect 293T cells using an optimized dextran-mediated transfection method (Wu et al., "Addition of High Molecular Weight Dextran in Calcium Phosphate-mediated Transfection Significantly Improves Gene Transfer Efficiency," *Cell. Mol. Biol.* 53:67-74 (2007), which is hereby incorporated by reference in its entirety).

Figure 8:
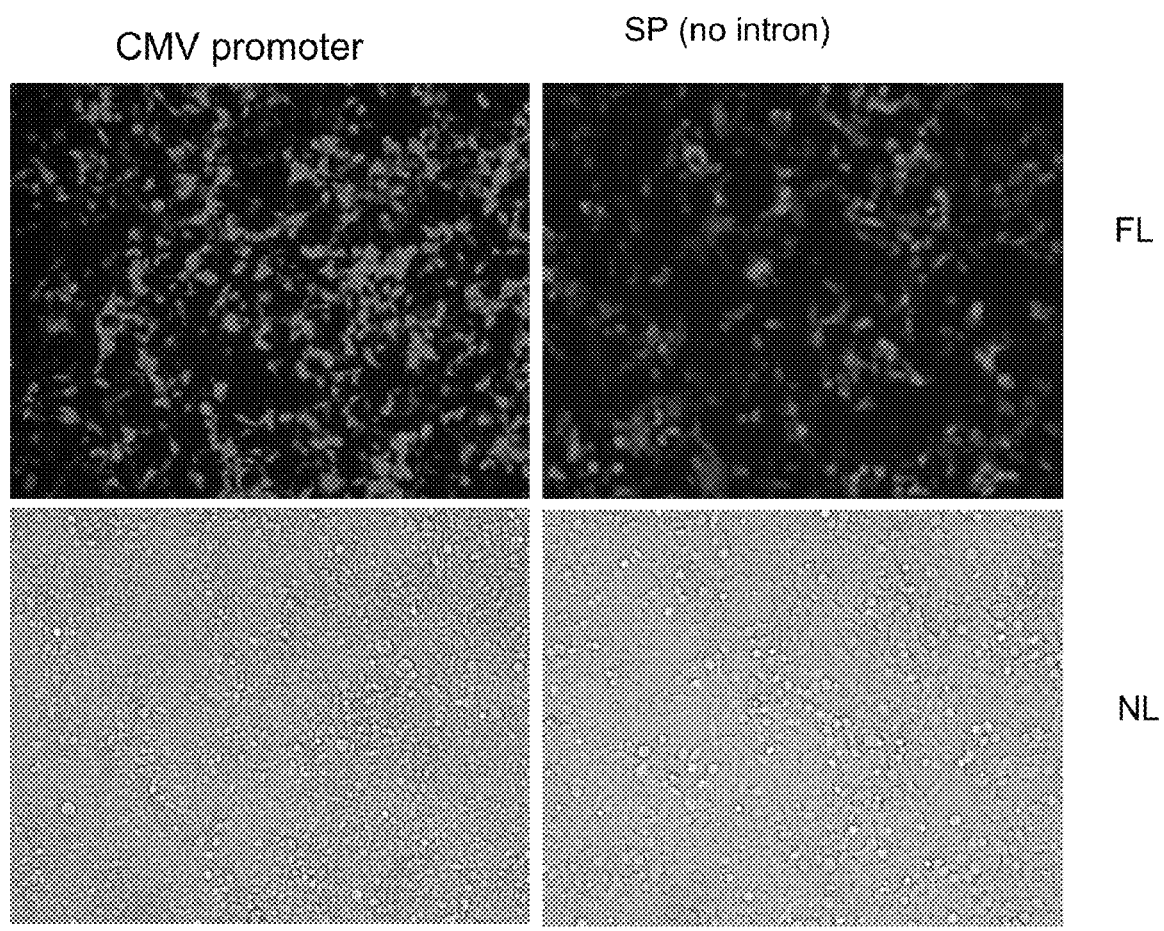
FIG. 8 provides four photomicrograph images showing red fluorescent protein (RFP) in 293 cells transfected with selected constructed plasmids. Photos were taken from the same microscopic field at 48-hour post transfection for each cell lines at magnification of 100X. FL=fluorescent light and NL=normal light. SP=shrimp promoter.
Figure 9A:
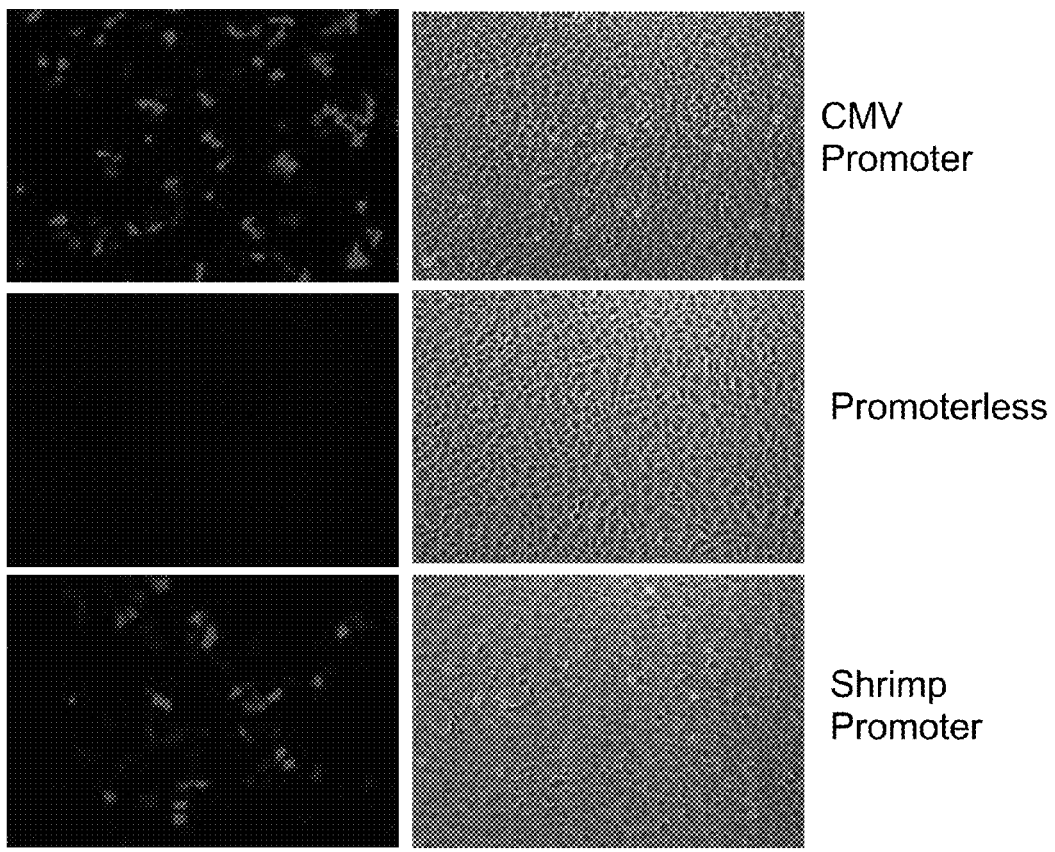
FIGS. 9A-D are photomicrographs showing red fluorescent protein (RFP) in different cells (Vero cells (FIG. 9A), CCO cells (FIG. 9B), EPC cells (FIG. 9C), and CHSE-214 cells (FIG. 9D)) transfected with selected constructed plasmids. Photos were taken from the same microscopic field at 24-hour post transfection time for each of these cell lines at magnification of 100X. FL=fluorescent light and NL=normal light.
Figure 9B:
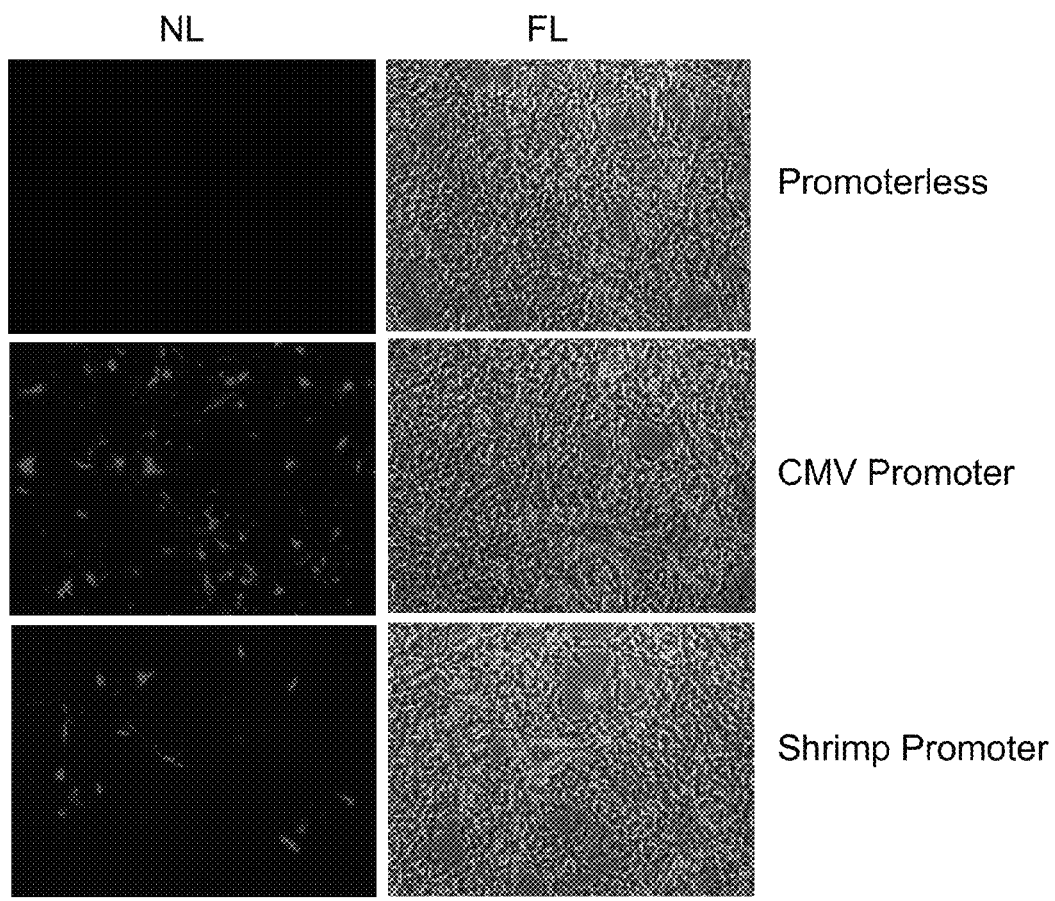
Figure 9C:
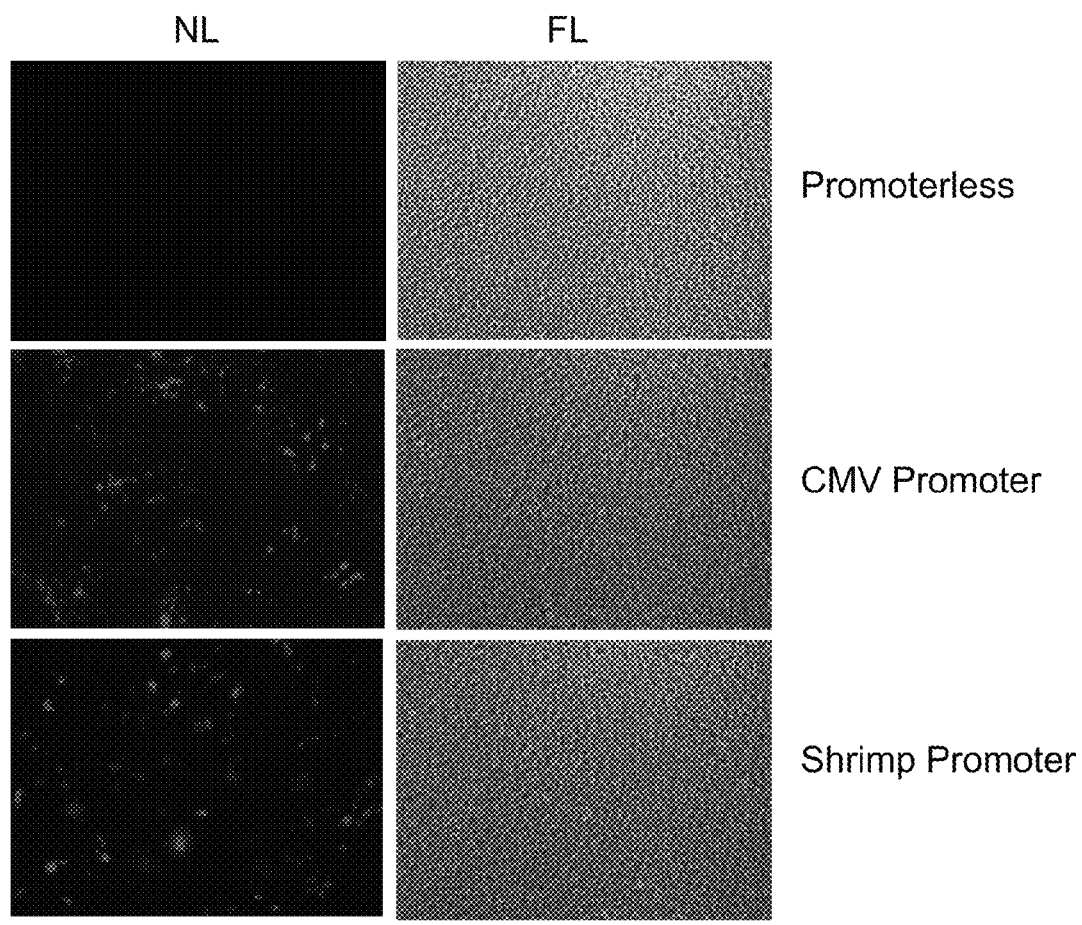
Figure 9D:
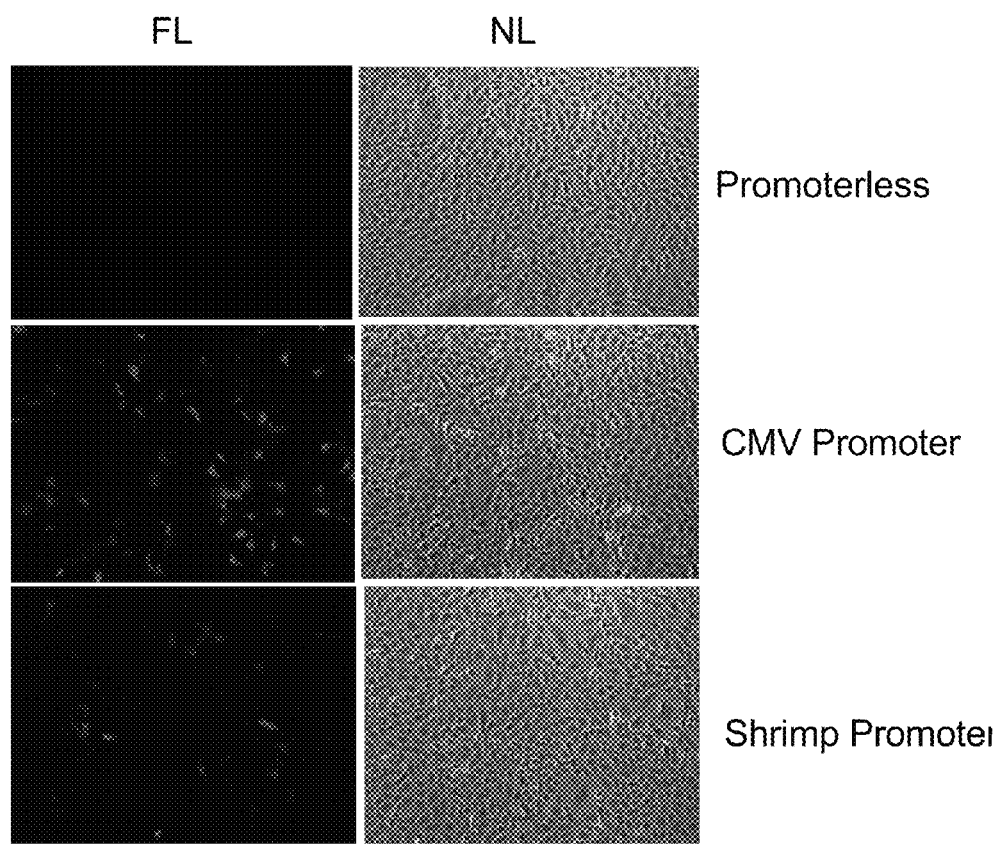

RFP expression in the transfected 293T cells was examined using an inverted fluorescent microscope. RFP expression from both shrimp and CMV promoters were observed and compared (FIG. 8).

Transfection of Other Five Cell Lines

Cell lines. The pAAV β-actin-P-mRFP construct was also tested for the RFP expression in other cell lines including Vero (Africa monk kidney cells) and four cell lines established from aquatic animals: EPC (grass carp epithelioma papulosum cyprini), CHSE-214 (chinook salmon embryo), GFP (grass carp fins), and CCO (channel catfish ovarian).

Cell plating. 24 hours prior to transfection, test cells at exponential growth phase were harvested and seeded to a density of $2\times10^5$ cells per T-12.5 cm$^2$ flask and grown overnight in complete growth medium to obtain 50-70% confluence the following day.

Complex formation. Into a sterile tube, 6.0 μl TransIT-LT1 transfection reagent was added directly into 200 μl of serum free medium and mixed completely by gentle pipetting, incubated at room temperature (RT) for 20 minutes, then 2.0 μg of plasmid DNA (2-5 μl) was added to the diluted TransIT-LT1 transfection reagent, mixed by gentle pipetting, and then incubated at RT for an additional 30 minutes.

Transfection of cells. Immediately before transfection, the medium of the cells prepared for transfection was changed with warmed fresh medium (2.5 ml/flask). The TransIT LT1 reagent/DNA complex mixture was added drop-wise to the cells in complete medium. Dishes were gently rocked to distribute the complexes evenly, incubated for 24-48 hours at the temperatures optimal for each cell culture, and checked for expression of RFP periodically (FIG. 9).

What is claimed:

1. An isolated β-actin nucleic acid promoter molecule from shrimp having a nucleotide sequence which is at least 90% similar to the nucleotide sequence of SEQ ID NO: 1.

2. The isolated nucleic acid promoter molecule according to claim 1, wherein the nucleic acid promoter molecule has a nucleotide sequence which is at least 95% similar to the nucleotide sequence of SEQ ID NO: 1.

3. The isolated nucleic acid promoter molecule according to claim 1, wherein the nucleic acid promoter molecule has a nucleotide sequence which is at least 99% similar to the nucleotide sequence of SEQ ID NO: 1.

4. A nucleic acid construct comprising:
a nucleic acid molecule encoding a protein;
the nucleic acid promoter molecule according to claim 1, wherein the nucleic acid promoter molecule is operably linked 5' to the nucleic acid molecule encoding a protein to induce transcription of the nucleic acid molecule encoding a protein; and
a 3' regulatory region operably linked to the nucleic acid molecule encoding a protein.

5. The nucleic acid construct according to claim 4, wherein the nucleic acid molecule encoding a protein has a sense orientation.

6. The nucleic acid construct according to claim 4, wherein the nucleic acid molecule encoding a protein has an antisense orientation.

7. An expression vector comprising:
the nucleic acid construct according to claim 4.

8. A host cell transduced with the nucleic acid construct according to claim 4.

9. The host cell according to claim 8, wherein the cell is selected from the group consisting of a bacterial cell, a yeast cell, an insect cell, and a crustacean cell.

10. The host cell according to claim 9, wherein the crustacean cell is a shrimp cell.

11. A nucleic acid expression cassette comprising:
the β-actin promoter molecule according to claim 1;
a multiple cloning site positioned in the nucleic acid construct to permit insertion of a nucleic acid molecule encoding a protein, whereby the nucleic acid molecule is transcribed;
an operable termination segment; and
a nucleic acid molecule encoding a detectable marker.

12. The nucleic acid expression cassette according to claim 11, wherein the detectable marker is selected from the group consisting of green fluorescent protein, enhanced green fluorescent protein, β-galactosidase, and luciferase.

13. The expression vector of claim 7 that is a viral vector.

* * * * *

SEQUENCE LISTING

<160> NUMBER OF SEQ ID NOS: 17

<210> SEQ ID NO 1
<211> LENGTH: 1642
<212> TYPE: DNA
<213> ORGANISM: Litopenaeus vannamei

<400> SEQUENCE: 1

```
aaaatgaggc ggcggcaatg atttacgggc atatattcgg tcgaggagga cgaaatattc      60
tgaaatggaa cgaaagggga tgacgcggcg cggctctcgt cttcccgcct cgcattcaac     120
gctcggctcg accaatcagc ggccgagttt tgcgctatga ccatataagg cgatacgttt     180
gtccgggtgg ggtgggacga gccattgcgg cttatcgcgc gggggagtac cctctcaaaa     240
tgcactatgc actgccgtaa cactctttcg gaaagaatat ratacatcag tagatacctc     300
ttgaaaatta ggatccgatg cataccataa atccccaaat tagagagaat aaaaggggtt     360
aattcgatcg agagtaatga cacttggaac gacctcccct ctggagaaag tcgacgatcc     420
gagaggtgga gtaagcgccc tactcactct ctcactcgca gtccaacccg agaggaagca     480
gcacgtacgc tcgtccgccc tttgtaagta tagcctccca ttcgtccaag ttctgcaaat     540
attcgtgctt taagaaccac cctagtacat tattaagccc cagtgagatc ccaatcgtga     600
cccaaaatac gtaatttagc tgtaattcgc ccaaacttcg ccctcacgaa cctaccggcg     660
ctcgcatggg ggtgtgtcct ggaccgtccc caagtgtctt gcttacttca atgcgaaagt     720
tttcctcggg ggtttatata ccgactcgaa agtcacttca aggcttgttt tacactcgcc     780
cgttgaagtt tccccggggt agtggaggcg aaacaggtgt tctcagaaag gtcctatttt     840
tagtccccga gttgctcccc aactgtcaag tccaactcca aaagtaatga ttttagtggt     900
atttgatggt attttccag gctatttgtt ttattaagat tcttttttcat taattgggga     960 ttcgttgaat tttatatagt ccatttttac ttacgaagaa attgaaaatc cgattaatat    1020
gtgtaatgta agttaaatcg atcataataa tgtactaacg tgtaccacac tgctgaccgt    1080 tttctctta aataggagat taagaaagca aacttggtcc ggagacagca tgtaggcgag    1140
agaaagggag ggaggggaaa ggagaggaaa gagggggggt gggaggggta ggggggaggg    1200
aagtgcgtgt tgccggtgac gtcacgcttg gcttcatata atgtcggttt aggatgtcga    1260
ggcttcagtc taacacgggt actcgctctg tgcacaacgt cattcgggcc ggtcccgcaa    1320
cgccatatag tcagtgactg tgatattaac tcggtaaata acgtgatttg agtctctaat    1380
attttccccc ggattgtcgg gttttagtgt ggcacttgga tatcttttta atacttggtt    1440
caacgttatg gtggcttttgg gggatcatag tgacacttcg tgatagtgtg gtggtgaatg    1500
```

-continued

| aagctataca ataattgtga tttattggtg gatttttctc atgtggaaac actgttgtgg | 1560 |
| acatggatac gatttcttac ttgagtggct gtgcttaatc gcaactcttc cttccttaca | 1620 |
| gtagtaaaac aacaacaaca ag | 1642 |

<210> SEQ ID NO 2
<211> LENGTH: 18
<212> TYPE: DNA
<213> ORGANISM: Artificial
<220> FEATURE:
<223> OTHER INFORMATION: Primer LV-B-act-27-Se

<400> SEQUENCE: 2

| gagcccgaga ggaagcag | 18 |

<210> SEQ ID NO 3
<211> LENGTH: 24
<212> TYPE: DNA
<213> ORGANISM: Artificial
<220> FEATURE:
<223> OTHER INFORMATION: Primer LV-B-act-663-As

<400> SEQUENCE: 3

| cttcatcagg tagtctgtga ggtc | 24 |

<210> SEQ ID NO 4
<211> LENGTH: 24
<212> TYPE: DNA
<213> ORGANISM: Artificial
<220> FEATURE:
<223> OTHER INFORMATION: Primer iPCR out i1 Se

<400> SEQUENCE: 4

| attcgcctaa actccgccct cacg | 24 |

<210> SEQ ID NO 5
<211> LENGTH: 27
<212> TYPE: DNA
<213> ORGANISM: Artificial
<220> FEATURE:
<223> OTHER INFORMATION: Primer iPCR out i1 As

<400> SEQUENCE: 5

| tattttgggt cacgattggg gtctcac | 27 |

<210> SEQ ID NO 6
<211> LENGTH: 19
<212> TYPE: DNA
<213> ORGANISM: Artificial
<220> FEATURE:
<223> OTHER INFORMATION: Primer iPCR inr Ni1 Se

<400> SEQUENCE: 6

| cgccctcacg aacctaccg | 19 |

<210> SEQ ID NO 7
<211> LENGTH: 24
<212> TYPE: DNA
<213> ORGANISM: Artificial
<220> FEATURE:
<223> OTHER INFORMATION: Primer iPCR inr Ni1 As

<400> SEQUENCE: 7

| agaacttgga cgaatgggag gcta | 24 |

```
<210> SEQ ID NO 8
<211> LENGTH: 22
<212> TYPE: DNA
<213> ORGANISM: Artificial
<220> FEATURE:
<223> OTHER INFORMATION: Primer Fsbp-1

<400> SEQUENCE: 8
aaaatgaggc ggcggcaatg at                                              22

<210> SEQ ID NO 9
<211> LENGTH: 36
<212> TYPE: DNA
<213> ORGANISM: Artificial
<220> FEATURE:
<223> OTHER INFORMATION: Primer LV Bact Met-1 As

<400> SEQUENCE: 9
cttgttgttg ttgttttact actgtaagga aggaag                               36

<210> SEQ ID NO 10
<211> LENGTH: 24
<212> TYPE: DNA
<213> ORGANISM: Artificial
<220> FEATURE:
<223> OTHER INFORMATION: Primer LV BA i1J

<400> SEQUENCE: 10
atacttggaa agggcggacg agcg                                            24

<210> SEQ ID NO 11
<211> LENGTH: 27
<212> TYPE: DNA
<213> ORGANISM: Artificial
<220> FEATURE:
<223> OTHER INFORMATION: Primer LV BA PyRIM

<400> SEQUENCE: 11
actgcgagtg agagagtgag tagggcg                                         27

<210> SEQ ID NO 12
<211> LENGTH: 34
<212> TYPE: DNA
<213> ORGANISM: Artificial
<220> FEATURE:
<223> OTHER INFORMATION: Primer LV BA PyRIM34

<400> SEQUENCE: 12
gggttggact gcgagtgaga gagtgagtag ggcg                                 34

<210> SEQ ID NO 13
<211> LENGTH: 39
<212> TYPE: DNA
<213> ORGANISM: Artificial
<220> FEATURE:
<223> OTHER INFORMATION: Primer LV BA PyRIM39S

<400> SEQUENCE: 13
agagtgagag agtgagagag tgagagagtg agtagggcg                            39

<210> SEQ ID NO 14
<211> LENGTH: 55
<212> TYPE: DNA
<213> ORGANISM: Artificial
<220> FEATURE:
<223> OTHER INFORMATION: Primer LV BA PyRIM55S
```

```
<400> SEQUENCE: 14
agagtgagag agtgagagag tgagagagtg agagagtgag agagtgagta gggcg          55

<210> SEQ ID NO 15
<211> LENGTH: 16
<212> TYPE: DNA
<213> ORGANISM: Artificial
<220> FEATURE:
<223> OTHER INFORMATION: Primer M13 F

<400> SEQUENCE: 15
gtaaaacgac ggccag                                                    16

<210> SEQ ID NO 16
<211> LENGTH: 17
<212> TYPE: DNA
<213> ORGANISM: Artificial
<220> FEATURE:
<223> OTHER INFORMATION: Primer M13 R

<400> SEQUENCE: 16
caggaaacag ctatgac                                                   17

<210> SEQ ID NO 17
<211> LENGTH: 24
<212> TYPE: DNA
<213> ORGANISM: Artificial
<220> FEATURE:
<223> OTHER INFORMATION: Primer Rsbp-1

<400> SEQUENCE: 17
tacaaccagg gcggctactt cgtc                                           24
```